(12) United States Patent
Jenson et al.

(10) Patent No.: US 9,282,955 B2
(45) Date of Patent: Mar. 15, 2016

(54) TISSUE PUNCTURE CLOSURE DEVICE

(71) Applicant: BOSTON SCIENTIFIC SCIMED, INC., Maple Grove, MN (US)

(72) Inventors: Mark L. Jenson, Greenfield, MN (US); Jason P. Hill, Brooklyn Park, MN (US); Joseph Thielen, Buffalo, MN (US); Michael J. Pikus, Golden Valley, MN (US); Joel Groff, Montrose, MN (US); David Hill, Long Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 62 days.

(21) Appl. No.: 13/964,088

(22) Filed: Aug. 11, 2013

(65) Prior Publication Data

US 2013/0325060 A1    Dec. 5, 2013

Related U.S. Application Data

(63) Continuation of application No. 12/948,569, filed on Nov. 17, 2010, now Pat. No. 8,529,598, which is a continuation-in-part of application No. 12/390,241, filed on Feb. 20, 2009, now Pat. No. 8,317,824.

(51) Int. Cl.
| | |
|---|---|
| *A61B 17/03* | (2006.01) |
| *A61B 17/10* | (2006.01) |
| *A61B 17/00* | (2006.01) |
| *A61B 17/04* | (2006.01) |
| *A61B 19/00* | (2006.01) |

(52) U.S. Cl.
CPC ......... *A61B 17/0057* (2013.01); *A61B 17/0467* (2013.01); *A61B 2017/00004* (2013.01); *A61B 2017/00455* (2013.01); *A61B 2017/00623* (2013.01); *A61B 2017/00637* (2013.01); *A61B 2017/00654* (2013.01); *A61B 2017/00663* (2013.01); *A61B 2017/00672* (2013.01); *A61B 2017/00898* (2013.01); *A61B 2019/4805* (2013.01)

(58) Field of Classification Search
CPC ................. A61B 17/0057; A61B 2017/00575; A61B 2017/00592; A61B 2017/00615; A61B 2017/00623; A61B 2017/00619; A61B 2017/00637; A61B 2017/00641; A61B 2017/00628
See application file for complete search history.

(56) References Cited

U.S. PATENT DOCUMENTS

| | | |
|---|---|---|
| 5,021,059 A | 6/1991 | Kensey et al. |
| 5,108,421 A | 4/1992 | Fowler |
| 5,129,882 A | 7/1992 | Weldon et al. |
| 5,192,300 A | 3/1993 | Fowler |
| 5,192,302 A | 3/1993 | Kensey et al. |
| 5,221,259 A | 6/1993 | Weldon et al. |

(Continued)

FOREIGN PATENT DOCUMENTS

| | | |
|---|---|---|
| EP | 1323450 B1 | 9/2004 |
| EP | 1568326 A1 | 8/2005 |

(Continued)

*Primary Examiner* — Christopher L Templeton
(74) *Attorney, Agent, or Firm* — Seager, Tufte & Wickhem LLP

(57) ABSTRACT

The present disclosure relates generally to methods and devices for closing and/or sealing an opening in a vessel wall and/or an adjacent tissue tract. In one illustrative embodiment, a device is provided for delivering and deploying an anchor, plug, filament, and locking element adjacent to the opening in the vessel wall and/or tissue tract.

4 Claims, 30 Drawing Sheets

(56) References Cited

U.S. PATENT DOCUMENTS

| | | |
|---|---|---|
| 5,222,974 A | 6/1993 | Kensey et al. |
| 5,254,105 A | 10/1993 | Haaga et al. |
| 5,275,616 A | 1/1994 | Fowler |
| 5,282,827 A | 2/1994 | Kensey et al. |
| 5,290,310 A | 3/1994 | Makower et al. |
| 5,292,332 A | 3/1994 | Lee |
| 5,310,407 A | 5/1994 | Casale et al. |
| 5,312,435 A | 5/1994 | Nash et al. |
| 5,320,639 A | 6/1994 | Rudnick |
| 5,342,393 A | 8/1994 | Stack |
| 5,350,399 A | 9/1994 | Erlebacher et al. |
| 5,370,660 A | 12/1994 | Weinstein et al. |
| 5,383,896 A | 1/1995 | Gershony et al. |
| 5,383,899 A | 1/1995 | Hammerslag et al. |
| 5,391,183 A | 2/1995 | Janzen et al. |
| 5,411,520 A | 5/1995 | Nash et al. |
| 5,413,571 A | 5/1995 | Katsaros et al. |
| 5,415,657 A | 5/1995 | Taymor-Luria |
| 5,419,765 A | 5/1995 | Weldon et al. |
| 5,437,631 A | 8/1995 | Janzen et al. |
| 5,441,517 A | 8/1995 | Kensey et al. |
| 5,443,481 A | 8/1995 | Lee et al. |
| 5,447,502 A | 9/1995 | Haaga |
| 5,454,833 A | 10/1995 | Boussignac et al. |
| 5,478,326 A | 12/1995 | Shiu et al. |
| 5,478,352 A | 12/1995 | Fowler |
| 5,486,195 A | 1/1996 | Myers et al. |
| 5,529,577 A | 6/1996 | Hammerslag et al. |
| 5,531,759 A | 7/1996 | Kensey et al. |
| 5,540,715 A | 7/1996 | Katsaros et al. |
| 5,545,178 A | 8/1996 | Kensey et al. |
| 5,549,633 A | 8/1996 | Evans et al. |
| 5,571,181 A | 11/1996 | Li |
| 5,573,518 A | 11/1996 | Haaga et al. |
| 5,591,204 A | 1/1997 | Janzen et al. |
| 5,593,422 A | 1/1997 | Muijs Van de Moer et al. |
| 5,601,602 A | 2/1997 | Fowler |
| 5,613,974 A | 3/1997 | Andreas et al. |
| 5,620,461 A | 4/1997 | Muijs Van De Moer et al. |
| 5,626,601 A | 5/1997 | Gershony et al. |
| 5,630,833 A | 5/1997 | Katsaros et al. |
| 5,649,959 A | 7/1997 | Hannam et al. |
| 5,653,730 A | 8/1997 | Hammerslag et al. |
| 5,662,681 A | 9/1997 | Nash et al. |
| 5,676,689 A | 10/1997 | Kensey et al. |
| 5,700,277 A | 12/1997 | Nash et al. |
| 5,707,393 A | 1/1998 | Kensey et al. |
| 5,716,375 A | 2/1998 | Fowler |
| 5,725,498 A | 3/1998 | Janzen et al. |
| 5,725,551 A | 3/1998 | Myers et al. |
| 5,728,114 A | 3/1998 | Evans et al. |
| 5,728,122 A | 3/1998 | Leschinsky et al. |
| 5,728,133 A | 3/1998 | Kontos |
| 5,728,134 A | 3/1998 | Barak |
| 5,741,223 A | 4/1998 | Janzen et al. |
| 5,782,860 A | 7/1998 | Epstein et al. |
| 5,810,884 A | 9/1998 | Kim |
| 5,830,130 A | 11/1998 | Janzen et al. |
| 5,843,124 A | 12/1998 | Hammerslag et al. |
| 5,853,421 A | 12/1998 | Leschinsky et al. |
| 5,861,004 A | 1/1999 | Kensey et al. |
| 5,871,474 A | 2/1999 | Hermann et al. |
| 5,871,501 A | 2/1999 | Leschinsky et al. |
| 5,906,631 A | 5/1999 | Imran |
| 5,916,236 A | 6/1999 | Muijs Van de Moer et al. |
| 5,922,009 A | 7/1999 | Epstein et al. |
| 5,935,147 A | 8/1999 | Kensey et al. |
| 5,947,997 A | 9/1999 | Pavcnik et al. |
| 5,948,425 A | 9/1999 | Janzen et al. |
| 5,951,583 A | 9/1999 | Jensen et al. |
| 5,957,952 A | 9/1999 | Gershony et al. |
| 6,007,561 A | 12/1999 | Bourque et al. |
| 6,017,359 A | 1/2000 | Gershony et al. |
| 6,045,569 A | 4/2000 | Kensey et al. |
| 6,045,570 A | 4/2000 | Epstein et al. |
| 6,048,357 A | 4/2000 | Kontos |
| 6,048,358 A | 4/2000 | Barak |
| 6,054,569 A | 4/2000 | Bennett et al. |
| 6,056,768 A | 5/2000 | Cates et al. |
| 6,056,769 A | 5/2000 | Epstein et al. |
| 6,056,770 A | 5/2000 | Epstein et al. |
| 6,066,146 A | 5/2000 | Carroll et al. |
| 6,080,183 A | 6/2000 | Tsugita et al. |
| 6,110,184 A | 8/2000 | Weadock et al. |
| 6,120,524 A | 9/2000 | Taheri |
| 6,126,675 A | 10/2000 | Shchervinsky et al. |
| 6,162,240 A | 12/2000 | Cates et al. |
| 6,179,863 B1 | 1/2001 | Kensey et al. |
| 6,183,496 B1 | 2/2001 | Urbanski |
| 6,190,400 B1 | 2/2001 | Van De Moer et al. |
| 6,261,309 B1 | 7/2001 | Urbanski |
| 6,296,632 B1 | 10/2001 | Lüscher et al. |
| 6,296,657 B1 | 10/2001 | Brucker |
| 6,296,658 B1 | 10/2001 | Gershony et al. |
| 6,325,789 B1 | 12/2001 | Janzen et al. |
| 6,350,274 B1 | 2/2002 | Li |
| 6,368,300 B1 | 4/2002 | Fallon et al. |
| 6,368,341 B1 | 4/2002 | Abrahamson |
| 6,425,911 B1 | 7/2002 | Akerfeldt et al. |
| 6,461,346 B1 | 10/2002 | Buelna |
| 6,464,712 B1 | 10/2002 | Epstein et al. |
| 6,468,293 B2 | 10/2002 | Bonutti et al. |
| 6,475,177 B1 | 11/2002 | Suzuki |
| 6,475,230 B1 | 11/2002 | Bonutti et al. |
| 6,500,152 B1 | 12/2002 | Illi |
| 6,508,828 B1 | 1/2003 | Akerfeldt et al. |
| 6,524,328 B2 | 2/2003 | Levinson |
| 6,527,734 B2 | 3/2003 | Cragg et al. |
| 6,537,299 B1 | 3/2003 | Hogendijk et al. |
| 6,540,735 B1 | 4/2003 | Ashby et al. |
| 6,569,187 B1 | 5/2003 | Bonutti et al. |
| 6,572,635 B1 | 6/2003 | Bonutti |
| 6,592,608 B2 | 7/2003 | Fisher et al. |
| 6,596,012 B2 | 7/2003 | Akerfeldt et al. |
| 6,596,014 B2 | 7/2003 | Levinson et al. |
| 6,613,070 B2 | 9/2003 | Redmond et al. |
| 6,623,509 B2 | 9/2003 | Ginn |
| 6,632,238 B2 | 10/2003 | Ginn et al. |
| 6,656,207 B2 | 12/2003 | Epstein et al. |
| 6,663,655 B2 | 12/2003 | Ginn et al. |
| 6,682,489 B2 | 1/2004 | Tenerz et al. |
| 6,685,727 B2 | 2/2004 | Fisher et al. |
| 6,699,261 B1 | 3/2004 | Cates et al. |
| 6,712,837 B2 | 3/2004 | Akerfeldt et al. |
| 6,733,515 B1 | 5/2004 | Edwards et al. |
| 6,743,195 B2 | 6/2004 | Zucker |
| 6,749,621 B2 | 6/2004 | Pantages et al. |
| 6,764,500 B1 | 7/2004 | Muijs Van De Moer et al. |
| 6,780,197 B2 | 8/2004 | Roe et al. |
| 6,786,915 B2 | 9/2004 | Akerfeldt et al. |
| 6,790,220 B2 | 9/2004 | Morris et al. |
| 6,818,008 B1 | 11/2004 | Cates et al. |
| 6,846,320 B2 | 1/2005 | Ashby et al. |
| 6,860,895 B1 | 3/2005 | Akerfeldt et al. |
| 6,863,680 B2 | 3/2005 | Ashby |
| 6,890,342 B2 | 5/2005 | Zhu et al. |
| 6,890,343 B2 | 5/2005 | Ginn et al. |
| 6,896,692 B2 | 5/2005 | Ginn et al. |
| 6,929,655 B2 | 8/2005 | Egnelöv et al. |
| 6,939,363 B2 | 9/2005 | Akerfeldt et al. |
| 6,942,684 B2 | 9/2005 | Bonutti |
| 6,955,683 B2 | 10/2005 | Bonutti |
| 6,964,658 B2 | 11/2005 | Ashby et al. |
| 6,969,397 B2 | 11/2005 | Ginn |
| 7,001,398 B2 | 2/2006 | Carley et al. |
| 7,008,439 B1 | 3/2006 | Janzen et al. |
| 7,008,440 B2 | 3/2006 | Sing et al. |
| 7,008,441 B2 | 3/2006 | Zucker |
| 7,008,442 B2 | 3/2006 | Brightbill |
| 7,025,776 B1 | 4/2006 | Houser et al. |
| 7,037,323 B2 | 5/2006 | Sing et al. |
| 7,044,916 B2 | 5/2006 | Tenerz et al. |
| 7,073,509 B2 | 7/2006 | Tenerz et al. |
| 7,083,635 B2 | 8/2006 | Ginn |

(56) References Cited

U.S. PATENT DOCUMENTS

| | | |
|---|---|---|
| 7,159,716 B2 | 1/2007 | Ashby et al. |
| 7,169,168 B2 | 1/2007 | Muijs Van De Moer et al. |
| 7,192,436 B2 | 3/2007 | Sing et al. |
| 7,250,057 B2 | 7/2007 | Forsberg |
| 7,267,679 B2 | 9/2007 | McGuckin, Jr. et al. |
| 7,285,097 B2 | 10/2007 | Tenerz et al. |
| 7,316,704 B2 | 1/2008 | Bagaoisan et al. |
| 7,322,976 B2 | 1/2008 | Yassinzadeh |
| 7,331,979 B2 | 2/2008 | Khosravi et al. |
| 7,331,981 B2 | 2/2008 | Cates et al. |
| 7,335,220 B2 | 2/2008 | Khosravi et al. |
| 7,597,705 B2 | 10/2009 | Forsberg et al. |
| 7,611,479 B2 | 11/2009 | Cragg et al. |
| 7,618,436 B2 | 11/2009 | Forsberg et al. |
| 7,618,438 B2 | 11/2009 | White et al. |
| 7,621,937 B2 | 11/2009 | Pipenhagen et al. |
| 7,713,283 B2 | 5/2010 | Forsberg |
| 7,749,247 B2 | 7/2010 | Tegg |
| 7,749,248 B2 | 7/2010 | White et al. |
| 7,753,933 B2 | 7/2010 | Ginn et al. |
| 7,790,192 B2 | 9/2010 | Sawhney et al. |
| 7,837,705 B2 | 11/2010 | White et al. |
| 7,850,654 B2 | 12/2010 | Belhe et al. |
| 7,850,710 B2 | 12/2010 | Huss |
| 7,931,670 B2 | 4/2011 | Fiehler et al. |
| 7,931,671 B2 | 4/2011 | Tenerz |
| 7,993,365 B2 | 8/2011 | Morris et al. |
| 8,007,514 B2 | 8/2011 | Forsberg |
| 8,075,589 B2 | 12/2011 | Pipenhagen et al. |
| 8,083,768 B2 | 12/2011 | Ginn et al. |
| 8,105,352 B2 | 1/2012 | Egnelöv et al. |
| 8,109,945 B2 | 2/2012 | Boehlke |
| 8,118,831 B2 | 2/2012 | Egnelöv et al. |
| 8,128,652 B2 | 3/2012 | Paprocki |
| 8,133,238 B2 | 3/2012 | Maruyama et al. |
| 8,241,323 B2 | 8/2012 | Kawaura et al. |
| 8,262,683 B2 | 9/2012 | McFarlin et al. |
| 8,267,959 B2 | 9/2012 | Fällman et al. |
| 8,298,259 B2 | 10/2012 | Terwey |
| 8,337,522 B2 | 12/2012 | Ditter |
| 8,348,971 B2 | 1/2013 | Khanna et al. |
| 8,382,795 B2 | 2/2013 | Forsberg et al. |
| 8,398,675 B2 | 3/2013 | Egnelöv et al. |
| 8,465,517 B2 | 6/2013 | White et al. |
| 2005/0085853 A1 | 4/2005 | Forsberg et al. |
| 2005/0096696 A1 | 5/2005 | Forsberg |
| 2005/0096697 A1 | 5/2005 | Forsberg et al. |
| 2005/0125030 A1 * | 6/2005 | Forsberg et al. ............ 606/213 |
| 2005/0169974 A1 | 8/2005 | Tenerz et al. |
| 2005/0267521 A1 | 12/2005 | Forsberg |
| 2006/0004408 A1 | 1/2006 | Morris |
| 2006/0030866 A1 | 2/2006 | Schreck |
| 2006/0058844 A1 | 3/2006 | White et al. |
| 2006/0173492 A1 | 8/2006 | Akerfeldt et al. |
| 2007/0032824 A1 | 2/2007 | Terwey |
| 2007/0038244 A1 | 2/2007 | Morris et al. |
| 2007/0038245 A1 | 2/2007 | Morris et al. |
| 2007/0083231 A1 | 4/2007 | Lee |
| 2007/0083232 A1 | 4/2007 | Lee |
| 2007/0135842 A1 | 6/2007 | Van de Moer et al. |
| 2008/0065121 A1 * | 3/2008 | Kawaura et al. ............ 606/146 |
| 2008/0097521 A1 | 4/2008 | Khosravi et al. |
| 2008/0109030 A1 | 5/2008 | Houser et al. |
| 2008/0114394 A1 | 5/2008 | Houser et al. |
| 2009/0024106 A1 | 1/2009 | Morris |
| 2010/0023051 A1 | 1/2010 | White et al. |
| 2010/0191280 A1 | 7/2010 | Forsberg |
| 2010/0217311 A1 | 8/2010 | Jenson et al. |
| 2010/0256555 A1 | 10/2010 | Birmelin et al. |

FOREIGN PATENT DOCUMENTS

| | | |
|---|---|---|
| EP | 1671591 A1 | 6/2006 |
| WO | 8911301 A1 | 11/1989 |
| WO | 2006078578 A2 | 7/2006 |
| WO | 2006124238 A2 | 11/2006 |
| WO | 2007037516 A2 | 4/2007 |
| WO | 2008135074 A1 | 11/2008 |
| WO | 2010129042 A1 | 11/2010 |

* cited by examiner

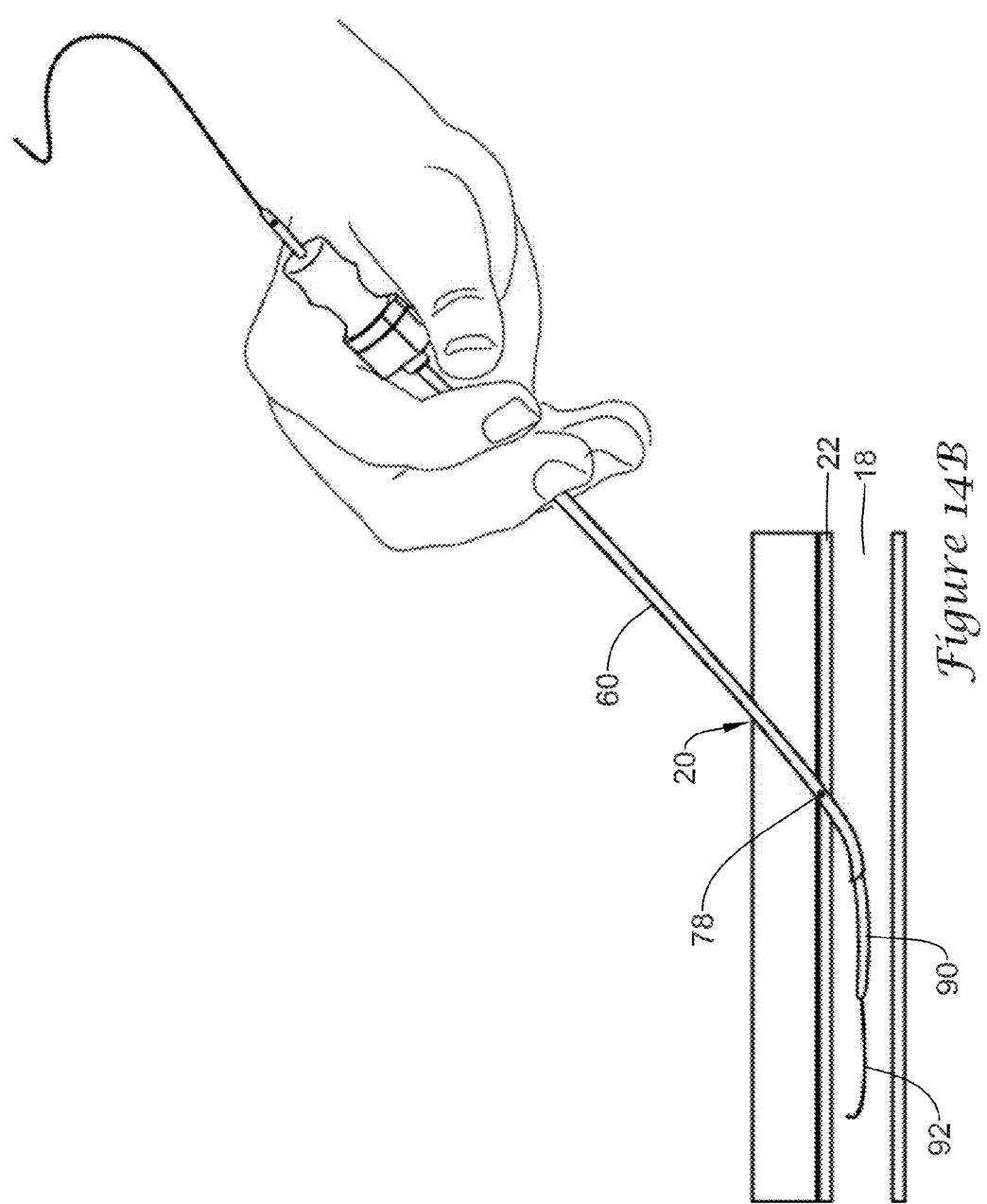

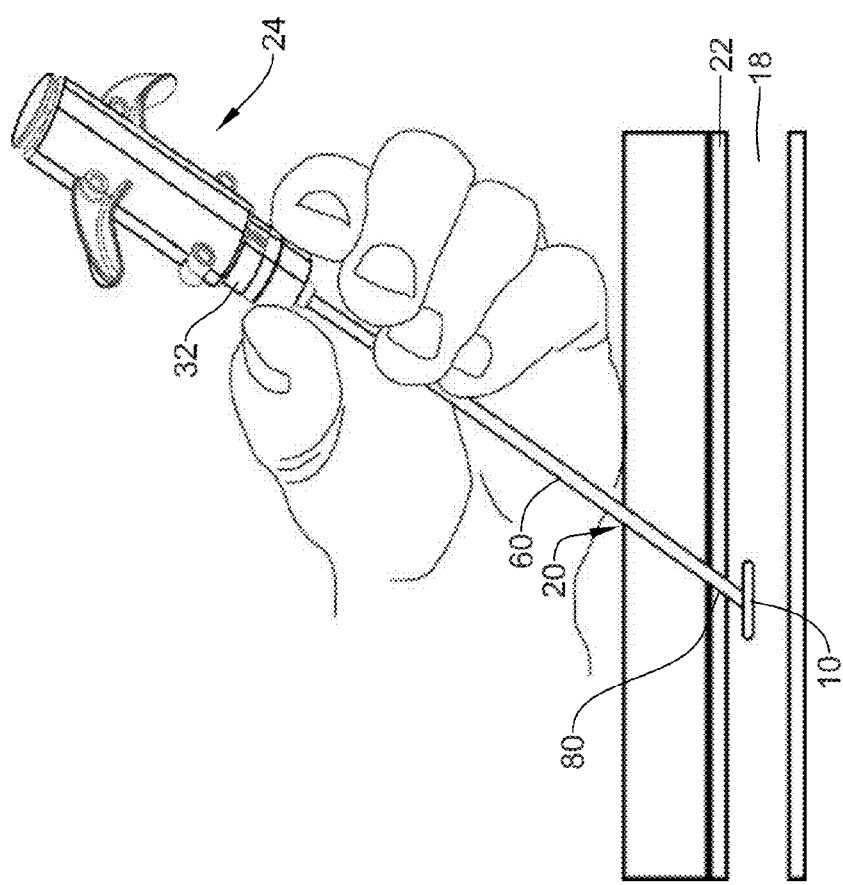

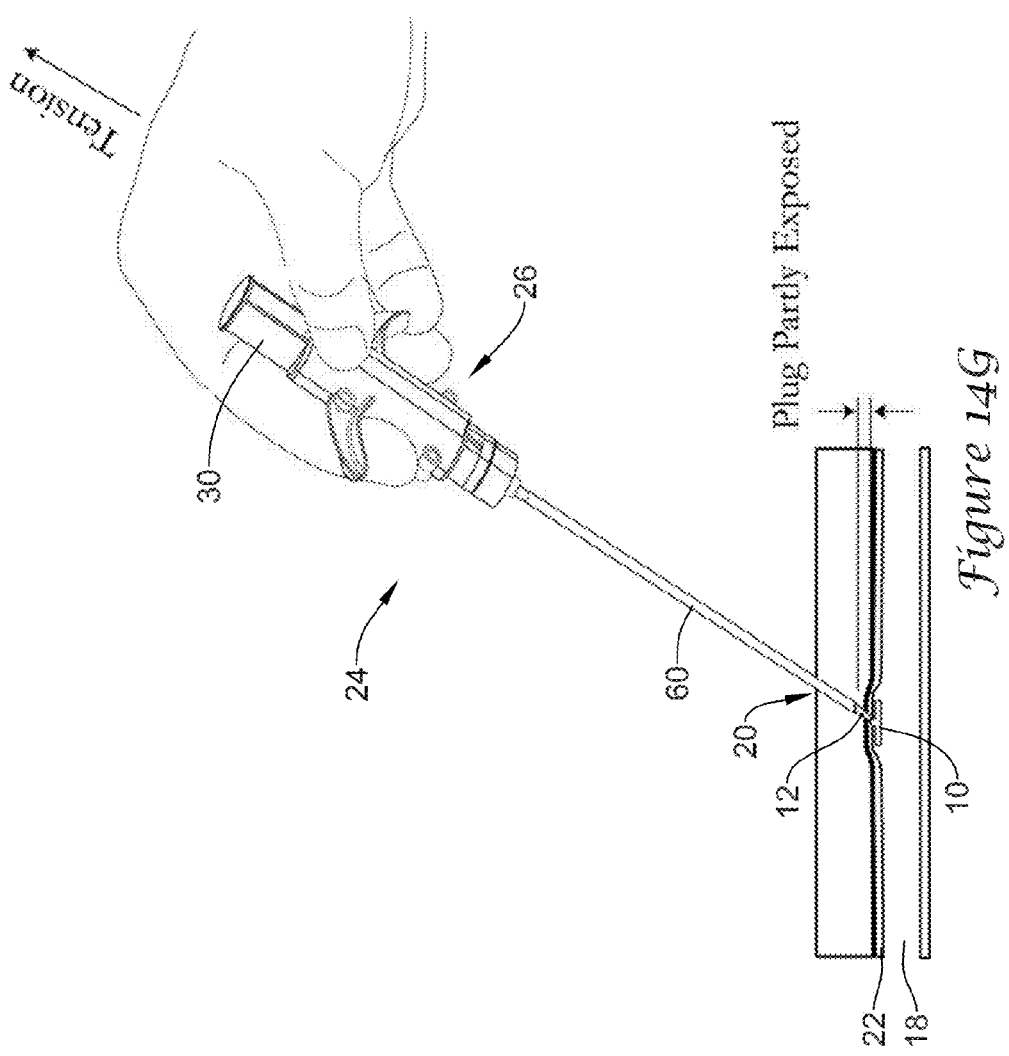

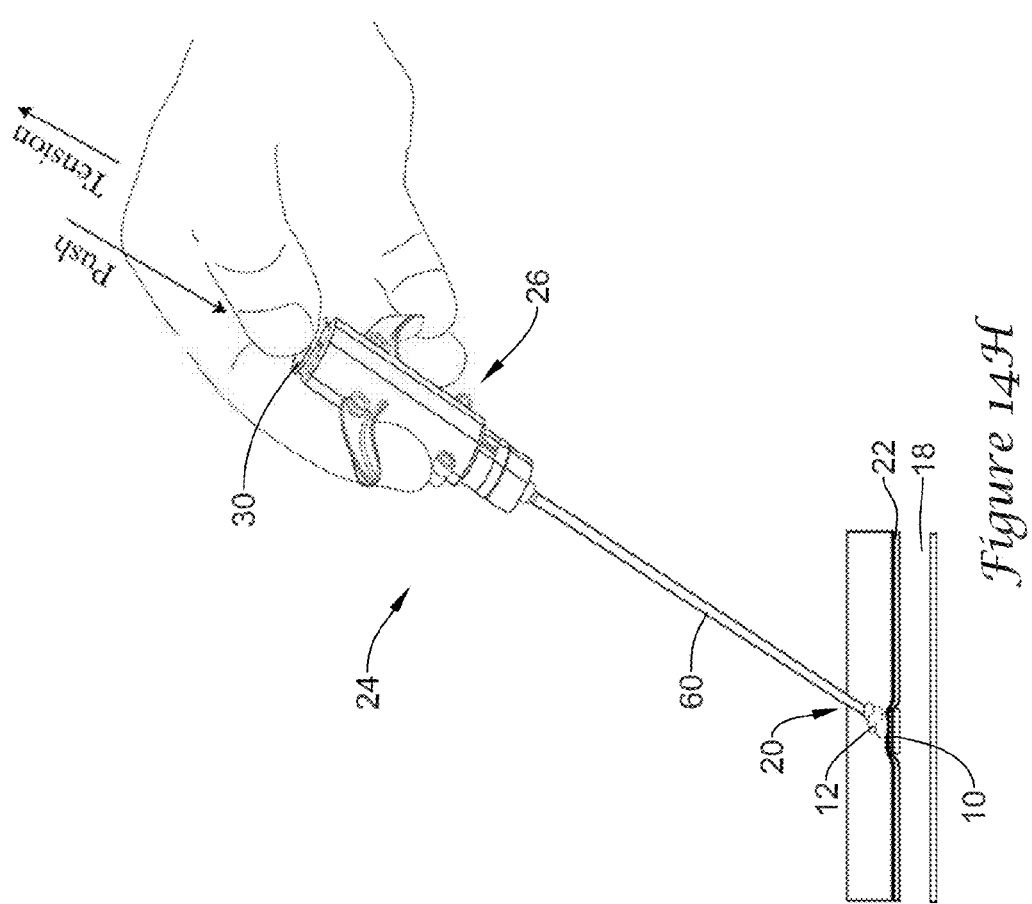

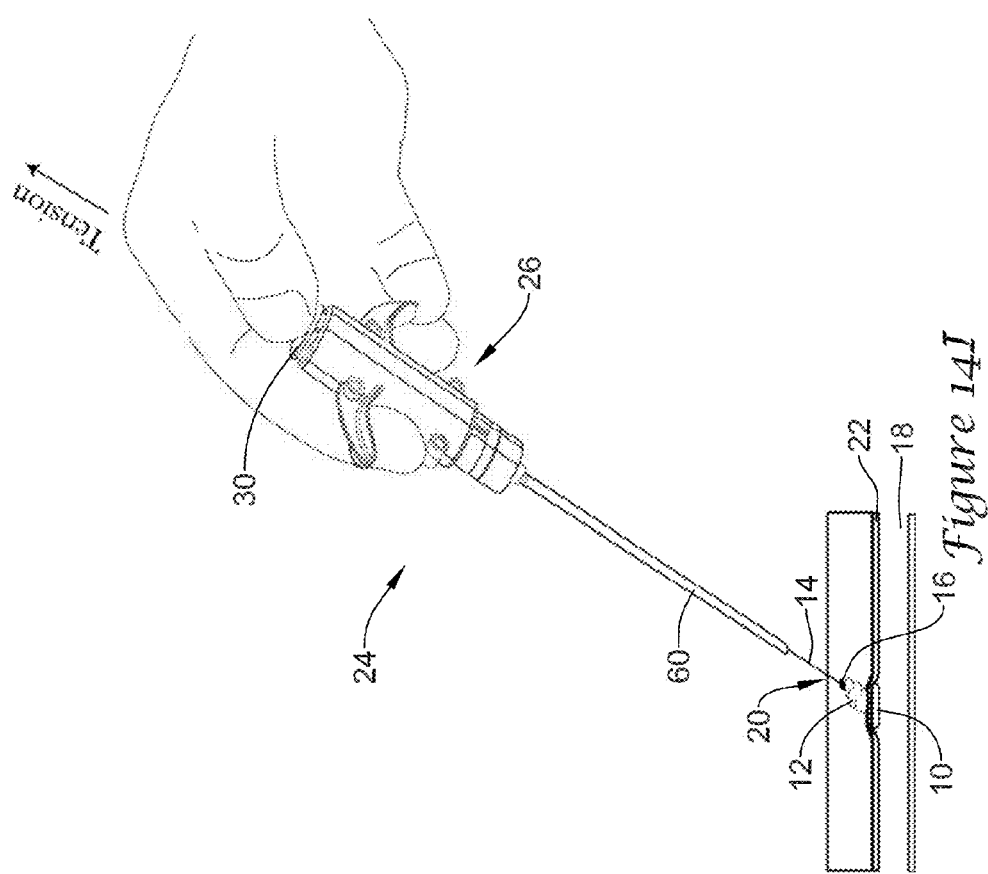

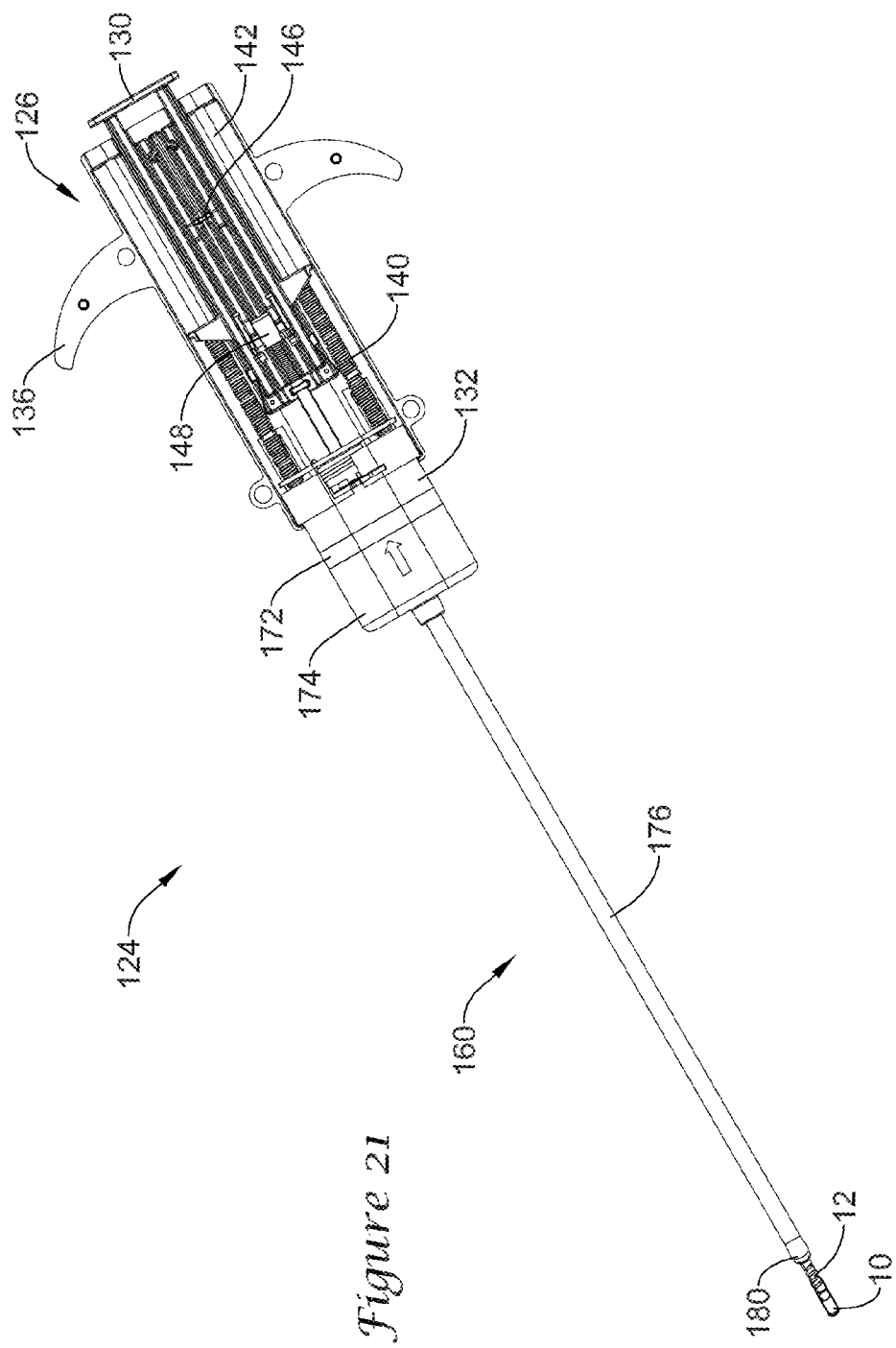

TISSUE PUNCTURE CLOSURE DEVICE

CROSS-REFERENCE TO RELATED APPLICATIONS

This application is a continuation of application Ser. No. 12/948,569, filed Nov. 17, 2010 now U.S. Pat. No. 8,529,598, which is a continuation-in-part of application Ser. No. 12/390,241, filed Feb. 20, 2009, now U.S. Pat. No. 8,317,824, which is incorporated by reference in its entirety herein.

FIELD

The present disclosure relates generally to medical devices and more particularly to methods and devices for closing and/or sealing punctures in tissue.

BACKGROUND

In many medical procedures, such as, for example, balloon angioplasty and the like, an opening can be created in a blood vessel or arteriotomy to allow for the insertion of various medical devices which can be navigated through the blood vessel to the site to be treated. For example, after initial access with a hollow needle, a guidewire may first be inserted through the tissue tract created between the skin, or the epidermis, of the patient down through the subcutaneous tissue and into the opening formed in the blood vessel. The guidewire is then navigated through the blood vessel to the site of the occlusion or other treatment site. Once the guidewire is in place, an introducer sheath can be slid over the guide wire to form a wider, more easily accessible, tract between the epidermis and the opening into the blood vessel. The appropriate medical device can then be introduced over the guidewire through the introducer sheath and then up the blood vessel to the site of the occlusion or other treatment site.

Once the procedure is completed, the medical devices or other equipment introduced into the vessel can be retracted through the blood vessel, out the opening in the blood vessel wall, and out through the tissue tract to be removed from the body. The physician or other medical technician is presented with the challenge of trying to close the opening in the blood vessel and/or the tissue tract formed in the epidermis and subcutaneous tissue. A number of different device structures, assemblies, and methods are known for closing the opening in the blood vessel and/or tissue tract, each having certain advantages and disadvantages. However, there is an ongoing need to provide new and improved device structures, assemblies, and/or methods for closing and/or sealing the opening in the blood vessel and/or tissue tract.

BRIEF SUMMARY

The following summary is provided to facilitate an understanding of some of the innovative features unique to the present disclosure and is not intended to be a full description. A full appreciation of the disclosure can be gained by taking the entire specification, claims, drawings, and abstract as a whole.

The present disclosure relates generally to medical devices and more particularly to methods and devices for closing and/or sealing punctures in tissue. In one illustrative embodiment, a device is provided for delivering and deploying an anchor, plug, filament, and a locking element adjacent to the opening in the vessel wall and/or tissue tract. In some cases, the plug may be configured to compress against the anchor when deployed in the tissue tract and/or opening in the vessel wall. In some cases, the filament may be automatically released from the device when the plug is compressed. In some cases, the device may include a mechanism to prevent premature compression of the plug.

BRIEF DESCRIPTION OF THE DRAWINGS

The disclosure may be more completely understood in consideration of the following detailed description of various embodiments of the invention in connection with the accompanying drawings, in which:

FIGS. 14A-J are perspective views showing an illustrative procedure for sealing and/or closing a puncture in a vessel wall and/or adjacent tissue tract using the implantation device of FIG. 2.

FIGS. 16-21 are perspective views and partial cut-away perspective views of the illustrative implantation device of FIG. 15 in various stages of a procedure for implanting the anchor, plug, filament, and locking element in the opening of the blood vessel or adjacent tissue tract.

Figure 1:
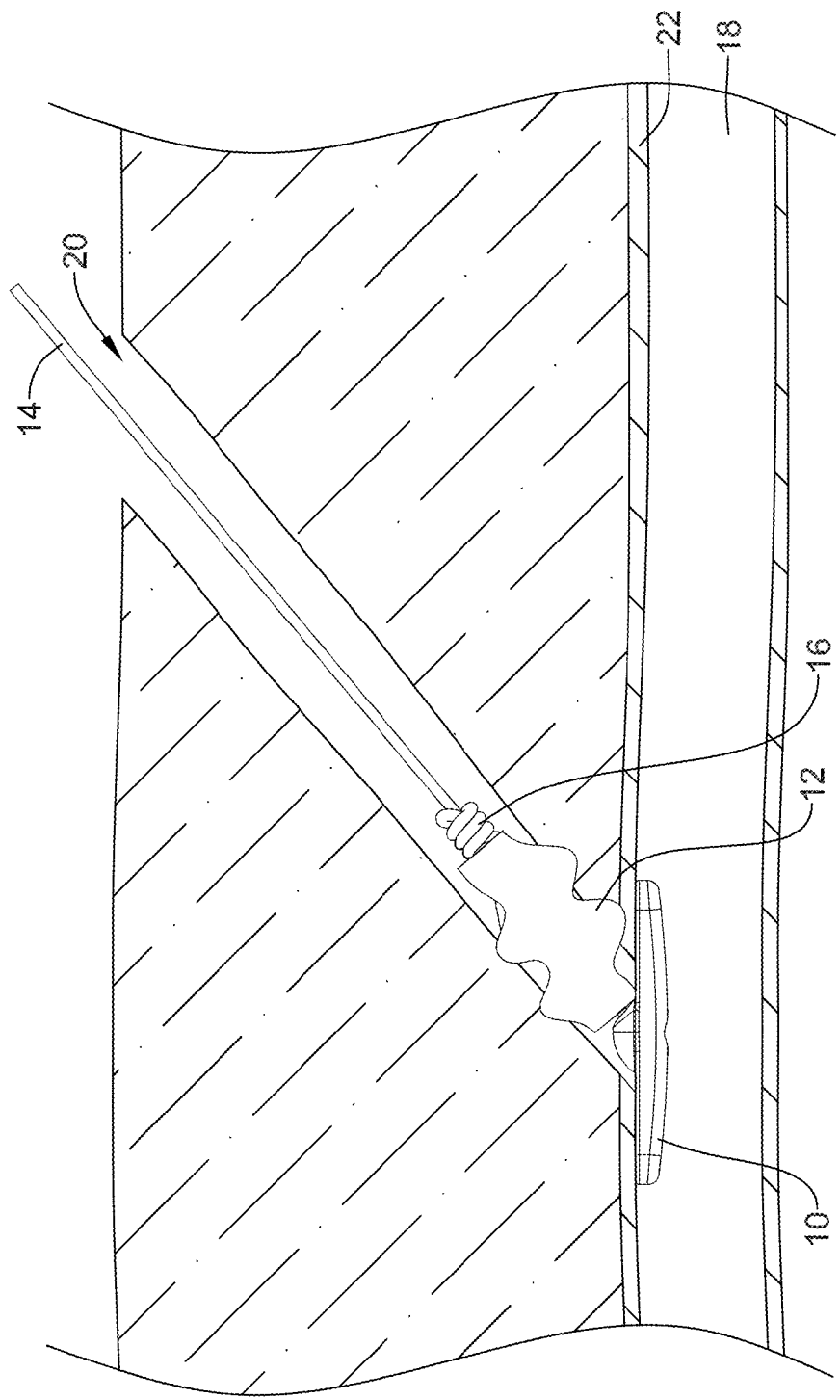
FIG. 1 is a schematic diagram of an illustrative embodiment of an anchor, a plug, a filament, and a locking element for closing and/or sealing an opening in a blood vessel and/or adjacent tissue tract.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a schematic diagram of an illustrative embodiment of an anchor 10, a plug 12, a filament 14, and a locking element 16 for closing and/or sealing an opening in a blood vessel 18 and/or adjacent tissue tract 20 that was created to gain access to the vessel 18 to perform a medical procedure. In the illustrative embodiment, the anchor 10 may be configured to engage an interior surface of the vessel wall 22. It should be noted that while the anchor 10 is illustrated with a dome-like feature protruding from the upper surface, this dome-like feature is not required, and the anchor 10 may be made without this feature, thereby having a substantially flat or slightly curved upper surface suitable for engaging the interior surface of the vessel wall 22. In some cases, the anchor 10 may be configured to partially or completely occlude the opening in the vessel wall 22, as desired. The anchor 10 may include a biodegradable material so that, over time, the anchor 10 is degraded, eroded, and/or absorbed in the body. In some cases, the anchor 10 may include a PLGA, PLLA, PGA or other degradable or erodable polymers, such as polyesters, polysaccharides, polyanhydrides, polycaprolactone, and various combinations thereof. In some cases, the anchor 10 may include a combination of the previously mentioned materials to impart a variable strength and/or degradation time profile in the anchor 10. One example anchor 10 that is configured to rapidly absorb and/or degrade is disclosed in Application Ser. No. 61/031,456, filed Feb. 26, 2008, which is hereby incorporated by reference. However, it is contemplated that any suitable anchor 10 may be used, as desired.

Filament 14 may include a proximal end, a distal end, with a length extending therebetween. The distal end of the filament 14 may be coupled to the anchor 10 with the filament 14 extending proximally therefrom and through the tissue tract 20. In some cases, the anchor 10 may include a raised portion including an eyelet to facilitate attachment of the distal end of the filament 14 to the anchor 10. In other cases, the distal end of the filament 14 may be molded into the anchor 10, passed through an opening in the anchor 10, or otherwise attached, connected, or secured to the anchor 10, as desired.

The filament 14 may include a biodegradable material so that, over time, the filament 14 is degraded, eroded, and/or absorbed in the body. In some cases, the filament 14 may include a PLGA, PLLA, PGA or other degradable or erodable polymers, such as polyesters, polysaccharides, polyanhydrides, polycaprolactone, and various combinations thereof. In some cases, the filament 14 can include a suture material, which may be a biodegradable suture.

Although the filament 14 is shown in FIG. 1 as having a distal end coupled to the anchor 10, it is contemplated that the filament 14 may be configured to loop through the anchor 10 in a pulley-like arrangement, if desired.

In the illustrative embodiment, the plug 12 can be disposed about at least a portion of the filament 14 adjacent to the anchor 10 in the tissue tract 20 and/or opening of the vessel wall 22. The plug 12 may be configured to fill the space in the tissue tract 20 adjacent to the vessel 18 and/or the opening in the vessel wall 22 to close and/or seal the vessel 18 opening and/or tissue tract 20. In some examples, the plug 12 may include a material that swells to fill space in the tissue tract 20 and/or vessel wall 22 opening, such as by elastic expansion, fluid absorption, chemical reaction, as well as any other suitable swelling and/or expansion. The plug 12 can be configured to promote hemostasis and/or clotting adjacent to the vessel 18. In one example, the plug 12 may include collagen foam, gelatin foam, PEG or other hydrogel, starch powder, any suitable hemostatic material, any suitable clot-promoting material, as well as any other suitable material, as desired. In some cases, other materials can be used to provide control of thrombogenicity or hydration.

In the illustrative embodiment, the plug 12 may be generally cylindrical in shape with a lumen extending therethrough. As illustrated, the plug 12 is shown in an axially compressed state after it has been deployed in the tissue tract 20. In some cases, the plug 12 can be radially compressed prior to delivery, as desired.

The plug 12 may include a biodegradable material so that, over time, the plug 12 is degraded, eroded, and/or absorbed in the body. In one example, the plug 12 can include an elongated member formed from gelatin foam, such as, for example, GELFOAM® (Pharmacia & Upjohn, Inc.—Bridgewater, N.J.) or Surgifoam™ (Johnson & Johnson—New Brunswick, N.J.). Other suitable examples of gelatin foam may include: CuraSpon® (CuraMedical BV—Assendelft, Netherlands), GelitaSpon® (Gelita Medical BV—Amsterdam, Netherlands), Gelaspon® (Juvalis—Bernburg, Germany). Additionally, collagen foam (such as that available from Integra LifeSciences—Plainsboro, N.J.) may be used in place of gelatin foam in some embodiments.

In some cases, the plug 12 can also include a hydrogel and/or a hemostatic material, if desired. Example hydrogels can include polyethylene glycols (PEG), including PEG 900, PEG 3350, and PEG 6000, as well as any other suitable hydrogel, as desired. Examples of hemostatic materials can include starch powders, such as BleedArrest™ Clotting Powder (Hemostasis, LLC—St. Paul, Minn.), PerClot™ (Starch Medical—San Jose, Calif.), SuperClot™ (Starch Medical—San Jose, Calif.), Arista™ AH (Medafor—Minneapolis, Minn.), or Vivastar® P (JRS Pharma GmbH+Co. KG—Rosenberg, Germany). In one illustrative example, the starch powder can be disposed in the gelatin or collagen foam material. In this illustrative example, the hydrogel can be coated on at least a portion of the gelatin or collagen foam material and starch powder combination by, for example, drip coating, spray coating, or dip coating. However, any other suitable method of combining the gelatin or collagen foam material, hydrogel, and starch powder can be used, as desired.

Some examples of plugs and plug materials that may be used in the closure device are disclosed in co-pending application Ser. No. 12/390,289, filed on Feb. 20, 2009, which is hereby incorporated by reference. In some cases, the plug 12 can include one or more voids, notches, slits, or other modifications to provide a desired axial compression of plug 12. Examples of plugs that may include voids, notches, slits, or other modification are disclosed in co-pending application Ser. No. 12/389,960, filed on Feb. 20, 2009, which is hereby incorporated by reference. In some cases, the illustrative plug 12 can be processed to have desired expansion characteristics. For example, the plug 12 can be tenderized to break down cell walls to increase the rate of expansion of the plug 12 and to reduce the force required to deliver the plug 12. Examples of plugs that have been tenderized or otherwise processed and methods of tenderizing or otherwise processing are disclosed in co-pending application Ser. No. 12/390,067, filed on Feb. 20, 2009, which is hereby incorporated by reference.

In the illustrative embodiment, one or more locking elements 16 can be used to help secure the plug 12 relative to the anchor 10. As illustrated, the locking element 16 can be disposed about at least a portion of the filament 14 proximal of the anchor 10. The locking element 16 can be configured to slide over the filament 14 and compress the plug 12 during deployment. In some cases, the locking element 16 can be slid distally over the filament 14 to compress the plug 12. In some cases, the locking element 16 can be a knot, such as a compression knot that may exert a radial force on the filament 14. As such, the knot may have a friction force of 0.5 pounds, 1 pound, 1.5 pounds, 2.0 pounds, 2.5 pounds, 3.0 pounds, or any other force depending on the production of the knot 16. In any event, the friction force of the knot 16 may be greater than the rebound force of the plug 12 to prevent the plug 12 axially expanding after axial compression.

In the illustrative embodiment, the locking element 16 may be separate and independent from the filament 14. In some cases, the locking element 16 may include a suture that is independent of the filament 14. In some cases, the suture of the locking element 16 may have a larger radial diameter than the filament 14 so that the locking element 16 has a sufficient size to contact the proximal end of the plug 12 for axial compression and not penetrating into the plug 12.

In other cases, the locking element 16 can be a sliding cinch, a disc shaped retainer, or other device. In some cases, the locking element 16 may be capable of sliding relative to the filament 14 upon an exertion of force. In other cases, the locking element 16 can be configured to slide in a distal direction relative to the filament 14, but not in a proximal direction. An example knot is disclosed in co-pending application Ser. No. 12/389,847, filed on Feb. 20, 2009, which is hereby incorporated by reference.

The locking element 16 may include a biodegradable material so that, over time, the locking element 16 is degraded, eroded, and/or absorbed in the body. In some cases, the locking element 16 may include a PLGA, PLLA, PGA or other degradable or erodable polymers, such as polyesters, polysaccharides, polyanhydrides, polycaprolactone, and various combinations thereof.

Figure 2:
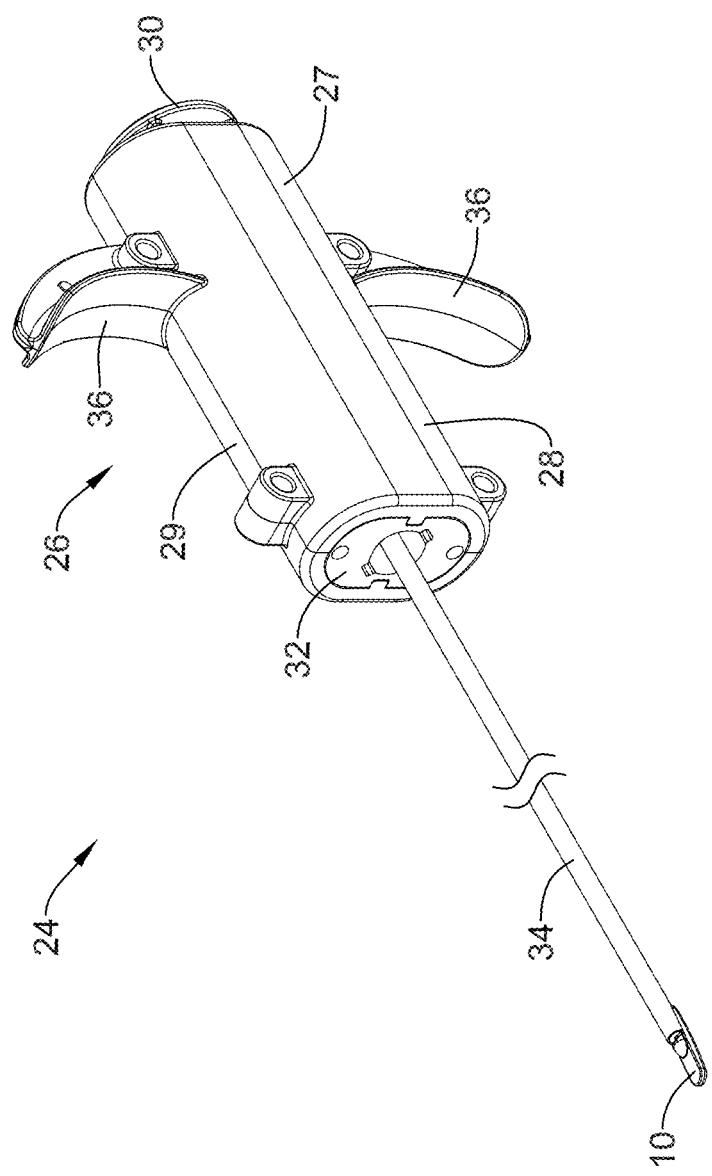
FIG. 2 is a perspective view of an illustrative embodiment of an implantation device for implanting the anchor, plug, filament, an/or locking element shown in FIG. 1 in the tissue tract and/or vessel.

FIG. 2 is a perspective view of an illustrative embodiment of an implantation device 24 for implanting the anchor 10, plug 12, filament 14, and locking element 16 shown in FIG. 1 in the tissue tract 20 and/or vessel 18. The illustrated implantation device 24 may be a generally syringe-shaped device having elongated components for introduction of the anchor 10, plug 12, filament 14, and locking element 16 into the opening in the vessel wall 22 and/or tissue tract 20.

The implantation device 24 may include a device handle 26 and a device sheath 34. The device sheath 34 may be a tubular member having a proximal end coupled to the device handle 26. The anchor 10 can be disposed adjacent the distal end of the device sheath 34, either within the device sheath 34, partially within the device sheath 34, or outside the device sheath 34, as shown. The plug 12, filament 14, and locking element 16 can also be disposed within the device sheath 34.

The device handle 26 can include a body portion 28 having a grip enhancement feature, such as one or more finger hooks 36 to assist the user in holding the implantation device 24. As illustrated, there are two finger hooks 36 provided on opposite sides of the device handle 26. However, it is contemplated that any or no grip enhancement feature may be used, as desired. The finger hooks 36 can be secured to or molded to the body portion 28 of the device handle 26, as desired. A proximal end of the device handle 26 may be configured to receive a plunger 30 therein. The device handle 26 may also include a control handle connector 32 configured to attach the implantation device 24 to an insertion sheath 60 (shown in FIG. 5). The illustrative implantation device 24 may allow for ambidextrous use and provided controlled deployment of the anchor 10, plug, 12, filament 14, and locking element 16.

Figure 3:
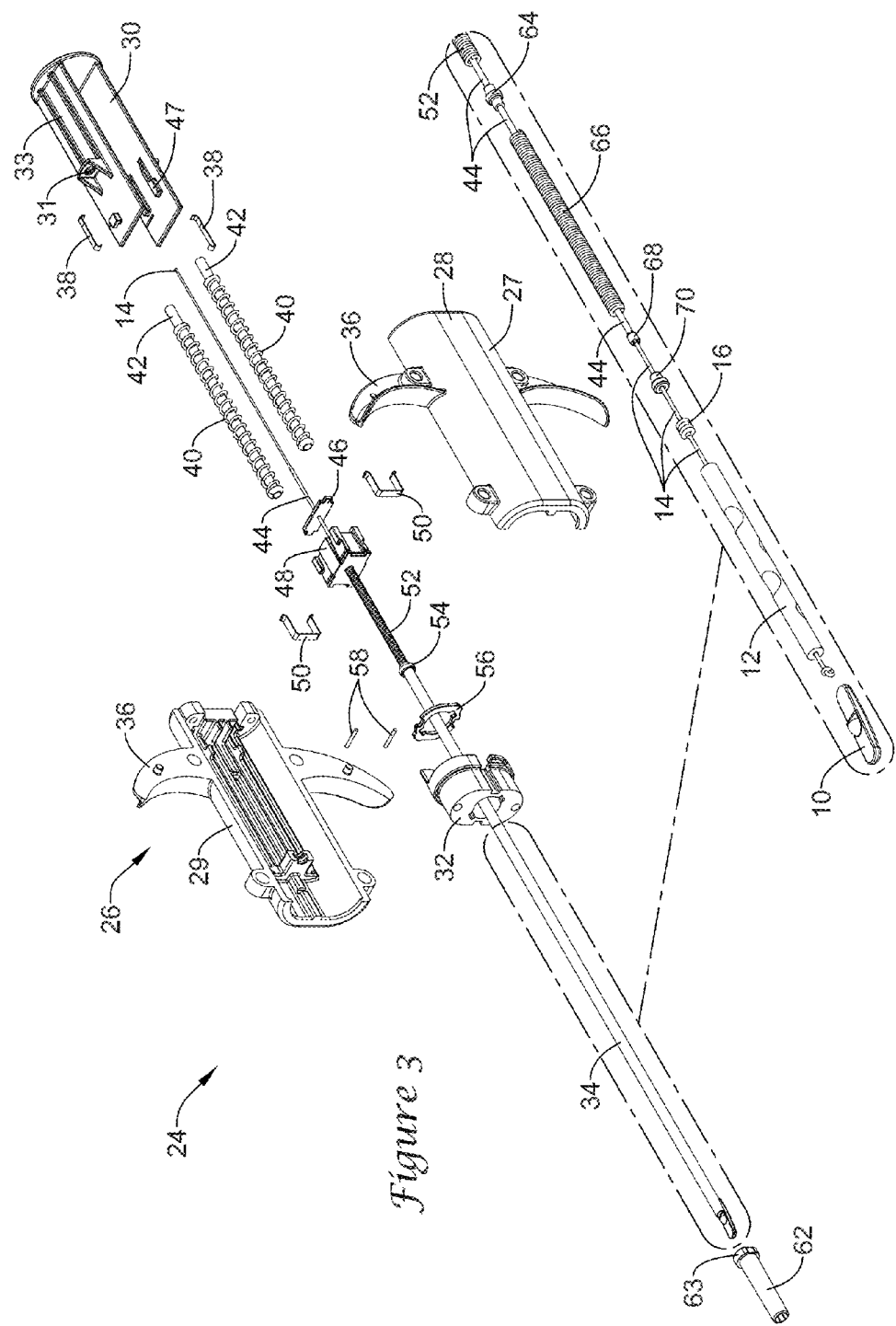
FIG. 3 is an exploded view of the illustrative implantation device of FIG. 2.

FIG. 3 is an exploded view of the illustrative implantation device 24 of FIG. 2. In the illustrative embodiment, the device handle 26 can include the handle body 28, the plunger 30, the control handle connector 32, as well as a number of other components to aid in deploying the anchor 10, plug 12, filament 14 and locking element 16 at a desired location. As illustrated, the handle body 28 may be a composite body including a first half 29 and a second half 27 secured together with a fastener, adhesive, or other method, as desired. However, this is not meant to be limiting and it is contemplated that any suitable composite or a non-composite structure may be used, such as, for example, a body molded as a single piece, as desired.

Plunger 30 may be configured to move relative to the handle body 28 to deploy the anchor 10, plug 12, filament 14, and locking device 16. In the illustrative example, the plunger 30 may move along one or more plunger guide pins 42, each of which may include an actuating spring 40 to bias the plunger 30 to a position outside of the handle body 28. The plunger guide pins 42 can be configured to have a free-floating first end, and a second end secured or mounted to the handle body 28. As illustrated, the plunger 30 may include a flange portion defining opening 31 configured to receive the one or more plunger guide pins 42. Plunger 30 may also include a ridge(s) or rib(s) 33 disposed along a length of the plunger 30 configured to help stiffen the plunger 30 and aid in guiding the plunger 30.

In the illustrative embodiment, the plunger 30 may be initially retained within the handle body 28 (as shown in FIG. 2) to help prevent accidental or premature deployment of the plug 12 and locking element 16. To retain the plunger 30 in the handle body 28, a plunger protection mechanism including one or more plunger retainer clips 38 and one or more plunger retainer clip pins 58 can be provided. The one or more plunger retainer clip pins 58 can be secured to the handle body 28. The one or more plunger retainer clips 38 can have a proximal end secured relative to the plunger 30 and a distal end configured to engage the plunger retainer clip pins 58. In some cases, the distal end of the plunger retainer clips 38 can be curved to wrap at least partially around the one or more plunger retainer clip pins 58. In some cases, the one or more plunger retainer clips 38 can be biased radially outward so that when the plunger retainer clips 38 are moved in a proximal direction relative to the one or more plunger retainer clip pins 58, the plunger retainer clips 38 disengage the one or more plunger retainer clip pins 58 and spring outward allowing the plunger 30 to move in a proximal direction to a position at least partially outside of the handle body 28. In some cases, when the plunger retainer clips 38 disengage the one or more plunger retainer clip pins 58, the actuating springs 40 can bias the plunger 30 to move out of the handle body 28.

The illustrative implantation device 24 can also include an interlock block 48 coupled to a proximal end of a proximal push rod 52. The interlock block 48 may also include one or more interlock block clips 50. The interlock block 48 and interlock block clips 50 may be configured to be disposed within the plunger 30 and slide relative to the plunger 30 until the plunger 30 is withdrawn a distance proximally so that the ramp 47 on plunger 30 may engage a proximal end of the interlock block 48 or interlock block clips 50. In some cases, the interlock block clips 50 may include an outwardly extending flange portion on a proximal end that may be configured to engage the ramp 47 of the plunger 30.

As illustrated, a tubular member 44 can be provided having a proximal end disposed in the device handle 26 and a distal end disposed in the device sheath 34. In one example, the tubular member 44 can be a collet, but any other suitable tubular member may be used, as desired. A proximal end of the collet 44 can be coupled to a retainer 46 configured to maintain the relative relationship of the collet 44 and handle body 28. The distal end of the collet 44 can include a collet lock ring 68 that is configured to have a releasable engagement with the filament 14. In some cases, the distal end of the collet 44 can be coupled to the proximal end of the filament 14. A filament release bead 64 can be disposed about a portion of the collet 44 a distance from the collet lock ring 68. The filament release bead 64 may slide relative to the collet 44 and is configured to engage the collet lock ring 68 and slide the collet lock ring 68 off of the collet 44 distal end releasing the filament 14.

A proximal push rod 52 can be disposed about at least a portion of the collet 44 between the interlock block 48 and the filament release bead 64. A distal push rod 66 can be disposed about the collet 44 and having a proximal end configured to engage the filament release bead 64 and a distal end configured to engage or couple a plug compression bead 70. The distal push rod 66 may be configured to slide over the collet lock ring 68. When the plunger 30 is actuated to deploy the plug 12 and locking element 16, the plunger 30 may engage the interlock block 48, which in turn may engage the proximal push rod 52, which in turn may engage the filament release bead 64, which in turn may engage the distal push rod 66, which in turn may engage the plug compression bead 70, which can engage the locking element 16, which can engage the proximal end of the plug 12. In this way, the force of the plunger 30 may be transferred to the locking element 16 to compress the plug 12. In some cases, the filament release bead 64 may simultaneously or concurrently pass over the collet 44 and engage the collet lock ring 68 to automatically release the filament 14 from the implantation device 24.

In the illustrative embodiment, the proximal push rod 52 and the distal push rod 66 may be a coil having a number of turns. However, it is contemplated that any suitable tubular member having a sufficient pushability and flexibility may be used, as desired.

Figure 5:
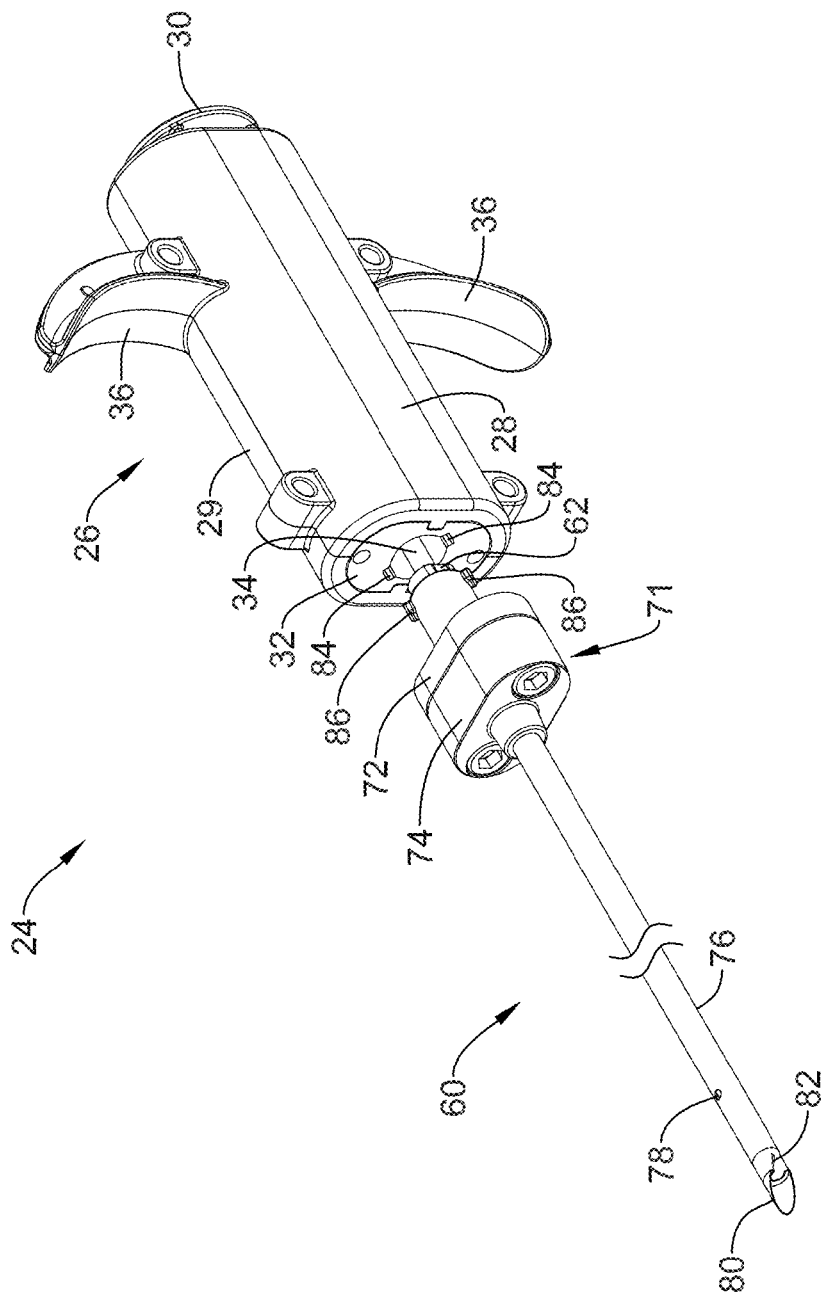

The implantation device 24 may also include a control handle connector 32 configured to engage a hub 71 of the insertion sheath 60 (shown in FIG. 5). The control handle connector 32 can be configured to be housed in the distal end of the handle body 28 or extend partially out of the distal end of the handle body 28. As illustrated, the control handle connector 32 may include a lumen configured to receive a proximal region of the device sheath 34. A control handle connector washer 56 can be embedded in the control handle connector 32.

The device sheath 34 may be configured to be coupled to the distal end of the handle 26 and extend distally therefrom. The device sheath 34 may include a thin-walled tubular member configured to house the collet 44, proximal push rod 52, filament release bead 64, distal push rod 66, collet lock ring 68, and plug compression bead 70. The device sheath 34 may also house the locking element 16, at least a portion of filament 14, and at least a portion of plug 12. The anchor 10 may be disposed adjacent to the distal end of the device sheath 34. As illustrated, a device sheath retainer 54 may be configured to couple the device sheath 34 relative to the control handle connector 32 and/or device handle 26, as desired.

In the illustrative embodiment, a bypass tube 62 is shown. The bypass tube 62 may be used to aid in loading the anchor 10 and device sheath 34 into the insertion sheath 60. For example, the anchor 10 may be arranged in a desired position for deployment and then loaded into the bypass tube 62. Then, when the implantation device 24 is to be loaded into a proximal end of the insertion sheath 60, the bypass tube 62 can be inserted into the proximal end of the insertion sheath 60 and allow the anchor 10 and device sheath 34 to pass out a distal end of the bypass tube 62. For example, the bypass tube 62 can include a proximal flange portion 63 that may be configured to engage the insertion sheath 60.

Figure 4:
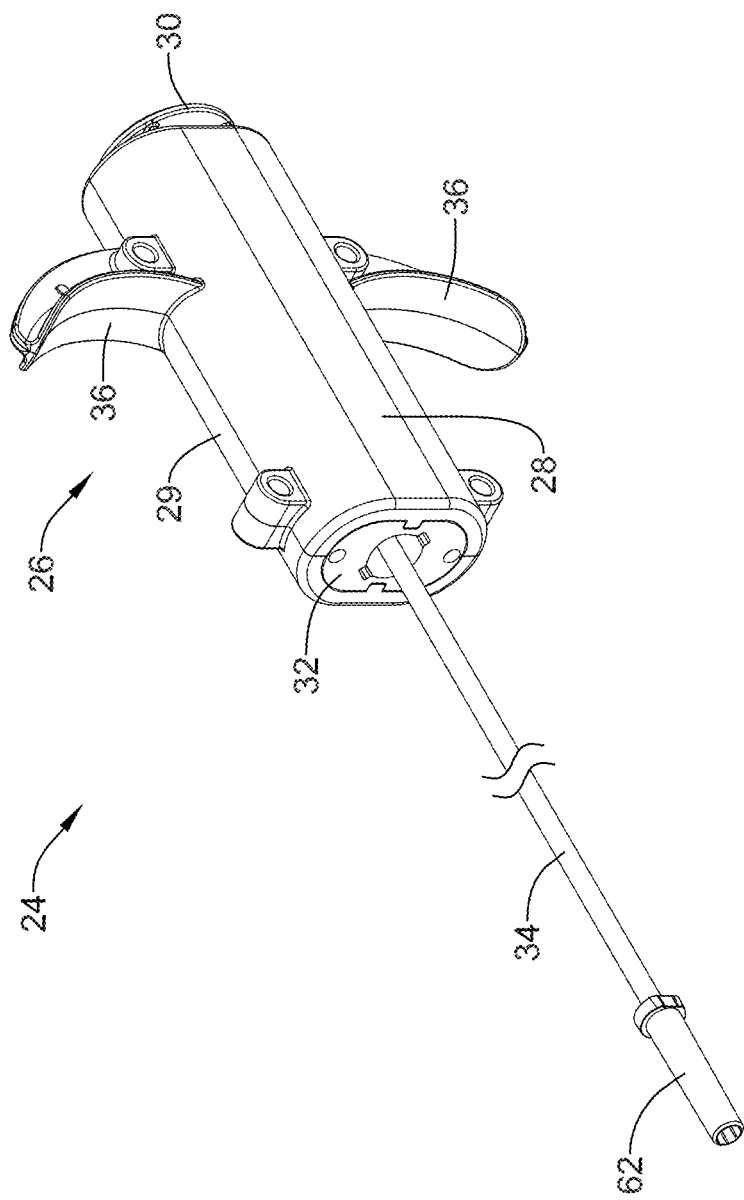
FIGS. 4-10 are perspective views and partial cut-away perspective views of the illustrative implantation device of FIG. 2 in various stages of a procedure for implanting the anchor, plug, filament, and locking element in the opening of the blood vessel or adjacent tissue tract.

FIGS. 4-10 are perspective views and partial cut-away perspective views of the illustrative implantation device 24 of FIG. 2 in various stages of a procedure for implanting the anchor 10, plug 12, filament 14, and locking element 16 in the opening in the blood vessel wall 22 and/or adjacent tissue tract 20. FIG. 4 is a perspective view of the illustrative implantation device 24 of FIG. 2 prior to being inserted into the insertion sheath 60. As illustrated, the anchor 10 (not shown in FIG. 4) and distal end of the device sheath 34 have been loaded into the bypass tube 62.

FIG. 5 is a perspective view of the illustrative implantation device 24 of FIG. 4 partially inserted into an insertion sheath 60. In the illustrative embodiment, the insertion sheath 60 may include a hub 71 and an insertion sheath tube 76. The hub 71 may be connected to a proximal end of the insertion sheath tube 76 and may include an insertion sheath connector 72, an insertion sheath cap 74, and a hemostatic seal (not shown) disposed between the insertion sheath connector 72 and insertion sheath cap 74. The insertion sheath connector 72 and insertion sheath cap 74 may be secured together with a fastener or adhesive, as desired. The hub 71 may have a lumen extending through the insertion sheath connector 72 and the insertion sheath cap 74. Alternatively, the hub 71 may be a single piece with a hemostatic seal disposed therein.

The insertion sheath tube 76 may include a thin-walled tubular member having a proximal end, a distal end, and a lumen extending therebetween. The proximal end of the insertion sheath tube 76 may be coupled to the hub 71 so that the lumen of the hub 71 is in fluid communication with the lumen of the insertion sheath tube 76. In some cases, the distal end of the insertion sheath tube 76 may be beveled to accommodate the anchor 10 at the desired deployment angle for proper approximation to the artery.

In some cases, a position indicator, such as opening 78 may be positioned adjacent to the distal end 80 of the insertion sheath tube 76 to aid in positioning the insertion sheath 60 at a desired location in the vessel. In some embodiments, two openings 78 may be provided, each on an opposing side of the insertion sheath tube 76. The opening 78 may provide an inlet for a bleed path which may flow through the insertion sheath 60 and/or a dilator to indicate the position of the insertion sheath 60 relative to the vessel wall opening. However, other suitable position indicators and/or locators may be used, such as, for example, one or more bent wires, one or more interlocking buttons, one or more folded components, an inflatable balloon, a radially expanding disc, as well as other suitable position indicators and/or locators or combinations thereof, as desired.

In some cases, the insertion sheath 60 may include an orientation indicator (not shown) on a proximal end thereof to help orient the insertion sheath 60. In some cases, the orientation indicator may be a line, mark, shape, other indicator, or combination thereof, to aid a user in orienting the insertion sheath 60 relative to its position in the vessel.

As illustrated, the device sheath 34 may be inserted in the proximal end of the lumen of the hub 71 and pass into the lumen of the insertion sheath tube 76. As illustrated, flange portion 63 of the bypass tube 62 may engage the proximal end of the hub 71 and be retained therein. Although not expressly shown in FIG. 5, the device sheath 34 may pass through the distal end of the bypass tube 62 and into the lumen of the insertion sheath tube 76. When the bypass tube 62 and/or device sheath 34 enters the insertion sheath 60, the device sheath 34 may pass through and open the hemostatic seal of the insertion sheath 60.

As illustrated, the insertion sheath connector 72 may include one or more pins and/or protrusions 86 that are configured to engage one or more slots 84 of the control handle connector 32 to mate the insertion sheath 60 to the implantation device 24. In the illustrative example, the control handle connector 32 of the device handle 26 may only mate with the insertion sheath connector 72 in only one orientation. As illustrated, the hub 71 may include a major radial axis that is offset from the major radial axis of the device handle 26.

Figure 6:
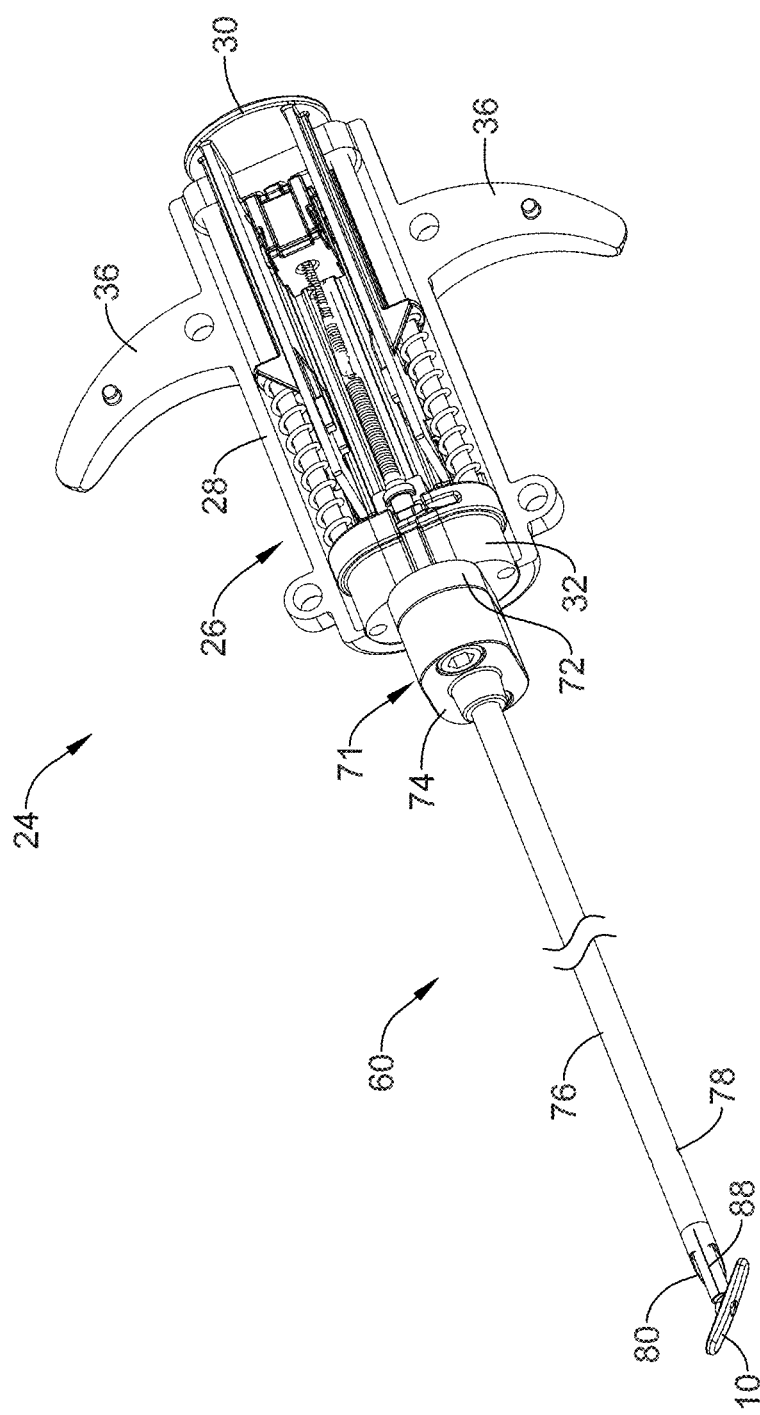

FIG. 6 is a partial cut-away perspective view of the illustrative implantation device 24 of FIG. 5 inserted in the insertion sheath 60. As illustrated, the implantation device 24 can be inserted into the insertion sheath 60 at an orientation offset from the insertion sheath 60, but this is not required. It is contemplated that other suitable connectors may be used instead of the illustrative control handle connector 32 and insertion sheath connector 72, as desired.

In the illustrated example, the device sheath 34 (not shown in FIG. 6) of the implantation device 24 may be completely inserted into the insertion sheath 60. As also shown in FIG. 6, when the implantation device 24 is completely inserted, the anchor 10 can be deployed out the distal end of the insertion sheath tube 76 into the vessel. When deployed, the anchor 10 may be initially spaced from the beveled distal end 80 of the insertion sheath tube 76, but, as shown in FIG. 7, can be subsequently retracted, in some cases automatically, against the beveled distal end 80.

Figure 7:
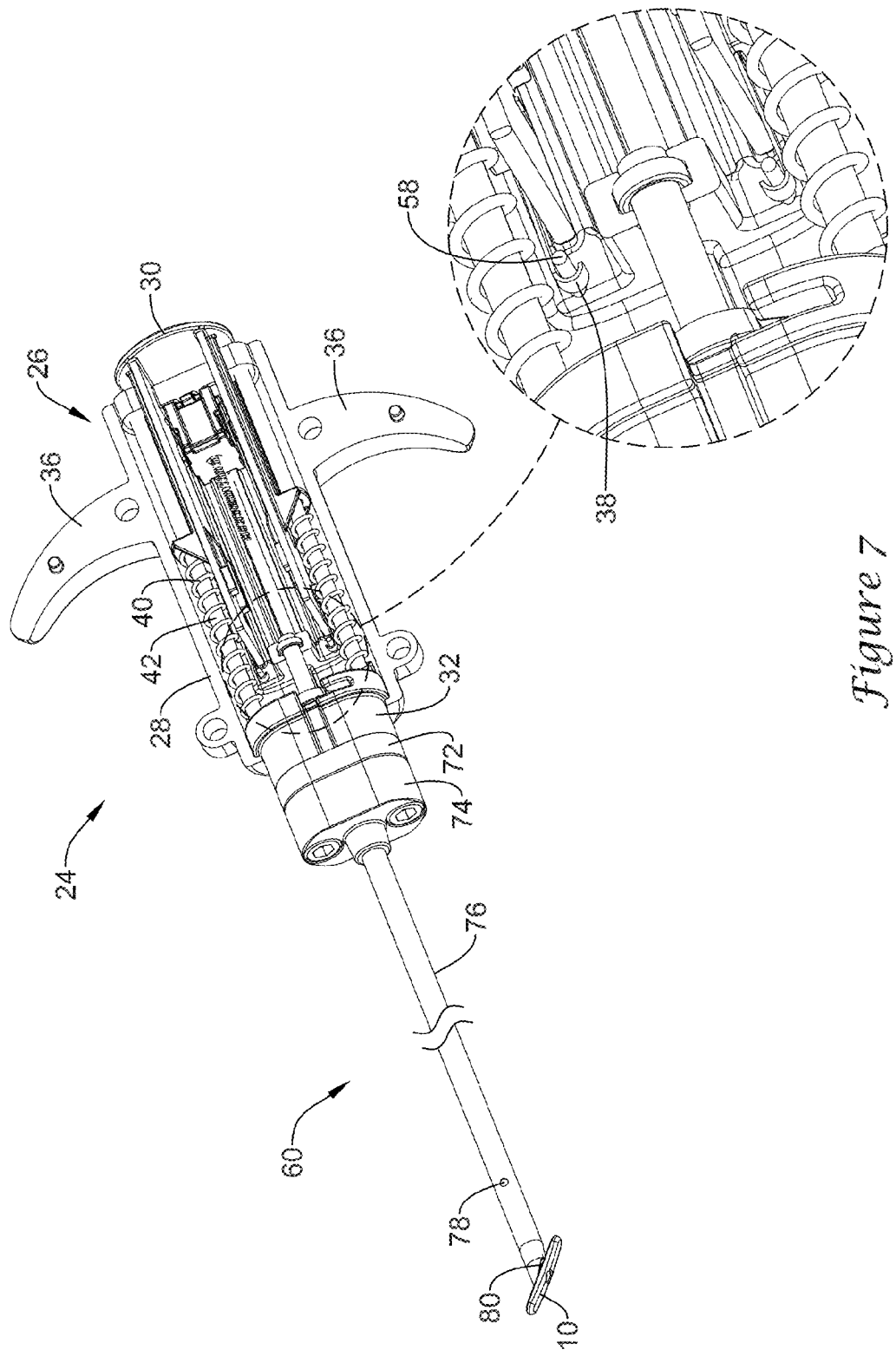

FIG. 7 is a partial cut-away perspective view of the illustrative implantation device 24 of FIG. 6 inserted in the insertion sheath 60. As illustrated, the implantation device 24 is secured to the insertion sheath 60. To do this, in one example, the device handle 26 of the implantation device 24 can be rotated relative to the insertion sheath 60 to align the insertion sheath connector 72 with the control handle connector 32. In the illustrative example, the implantation device 24 can be rotated about 90 degrees when viewed from the proximal end. The rotation may lock the control handle connector 32 to the insertion sheath connector 72. This rotation can release the control handle connector 32 from the housing body 28 moving the insertion sheath 60 distal relative to the implantation device 24 seating the anchor 10 against the beveled distal end 80 of the insertion sheath tube 76. Alternatively, the insertion sheath 60 may be held in a fixed position and the housing body 28 may move proximally relative to the insertion sheath 60 to seat the anchor 10 against the beveled distal end 80. The rotation may cause slots in the control handle connector washer 56 (not shown in FIG. 6 or 7) to align with slots in the control handle connector 32. The alignment may release the control handle connector 32 actuating the device handle 26 of the implantation device 24 proximally via the actuating springs 40. However, it is contemplated that other attachment, alignment, and/or release mechanisms may be used to connect the insertion sheath 60 to the implantation device 24 and to seat the anchor 10 against the beveled distal end 80 of the insertion sheath 60, as desired. Examples of such components that may be used can include interlocking snaps, torsion springs, spring releases, keys, push pins, and any other suitable component, as desired.

As shown in the blown up portion of FIG. 7, the plunger retainer clips 38 may be engaged to the plunger retainer clip pins 58 retaining the plunger 30 in a retracted state to prevent premature deployment.

Figure 8:
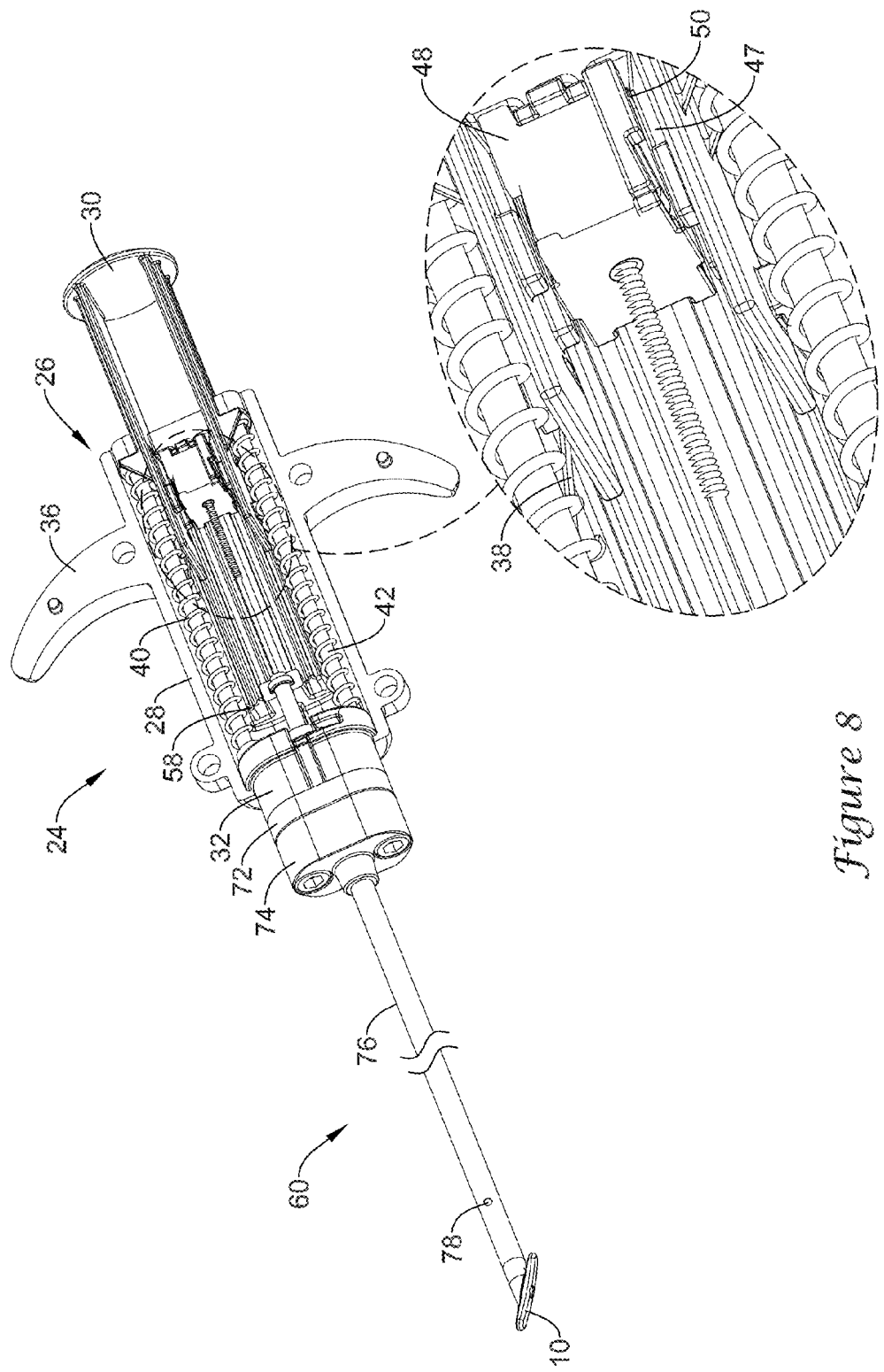

FIG. 8 is a partial cut-away perspective view of the illustrative implantation device 24 of FIG. 7 with the plunger 30 in a released position. In one example, to actuate the plunger 30 from the retracted state shown in FIG. 7 to the released position of FIG. 8, the plunger 30 may be depressed at least slightly causing the plunger retainer clips 38 (which can be biased radially outward) to disengage plunger retainer clip pins 58. When the plunger retainer clips 38 disengage the plunger retainer clip pins 58, the actuation springs 40 can cause the plunger 30 to move in a proximal direction. In some cases, a portion of the control handle connector 32 may hold the plunger retainer clips 38 against the plunger retainer clip pins 58 prior to the control handle connector 32 being activated and released from the handle body 28, thereby serving as an additional locking feature which functions as part of the plunger protection mechanism discussed above by preventing premature actuation of the plunger 30. However, the illustrative plunger protection mechanism including the control handle connector 32, plunger retainer clips 38, and plunger retainer clip pins 58 are merely illustrative and it is contemplated that any suitable plunger protection mechanism may be used, as desired. Further, it is contemplated that in some embodiments, the plunger 30 can be automatically actuated to the released position upon connection of the implantation device 24 to the insertion sheath 60 without the need for manual depression of the plunger 30, as desired.

In some embodiments, the implantation device 24 can be pulled proximally to seat the anchor 10 against the arteriotomy prior to proximal movement of the plunger 30 relative to the device handle 26. However, it is contemplated that the anchor 10 may be seated against the arteriotomy after releasing the plunger 30, if desired.

Figure 9:
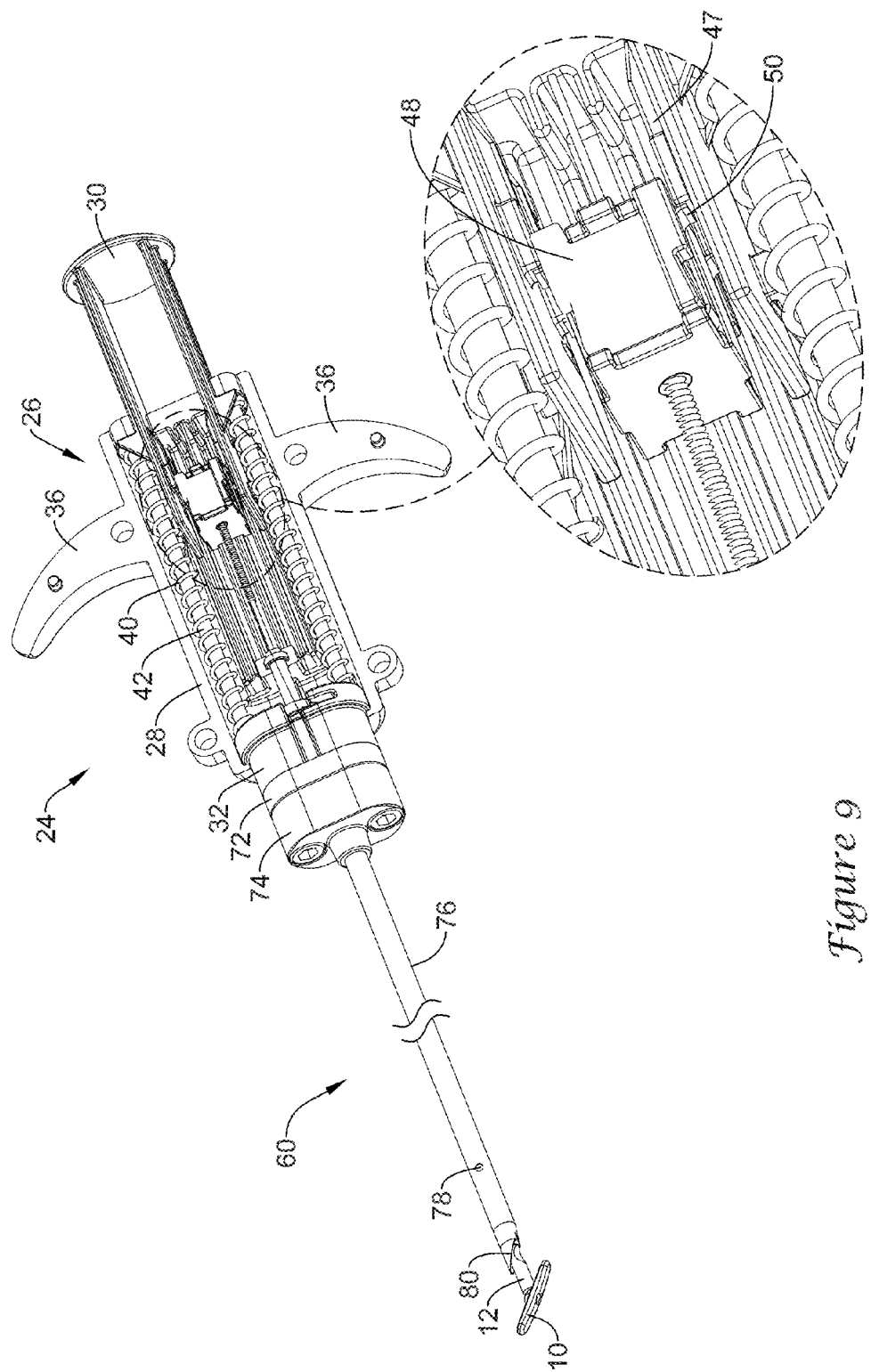

As illustrated in FIG. 8, the plunger 30 is shown in the released position from the device handle 26, but may still not be ready to deploy the anchor 10, plug 12, filament 14, and locking element 16 (elements 12, 14, and 16 are not shown in FIG. 8). In the illustrative embodiment, as noted above, the interlock block 48 and/or interlock block clips 50 may be configured to engage a ramp 47 or otherwise protruding portion of the plunger 30. To cause the interlock block 48 and/or interlock block clips 50 to engage the ramp 47, the plunger 30 may be moved proximally relative to the interlock block 48 and/or interlock block clips 50 causing the interlock block clips 50 to depress inward until the plunger 30 is moved proximally relative to the interlock block 48 so that the interlock block clips 50 may move radially outward to engage a proximal portion of the ramp 47, as shown in FIG. 9. In some cases, this relative movement can be accomplished by applying a tension to the device handle 26 of the implantation device 24 to retract the implantation device 24 and insertion sheath 60 in a proximal direction. The anchor 10 which is coupled to the filament 14 (not shown), which can be coupled directly or indirectly to the interlock block 48, can exert a counter force to the tension causing the interlock block 48 to slide distally relative to the device handle 26. Interlock block 48 may be formed from a metal, a polymer, or other suitable material, as desired. Interlock block clips 50 may be formed of a metal, a polymer, or other suitable material, as desired. Interlock block clips 50 may be formed of the same material as the interlock block 48, or may be formed from a different material.

As also shown in FIG. 9, the tension or proximal retraction of the implantation device 24 can also create a gap between the distal end 80 of the insertion sheath 60 and the anchor 10 providing a place for the plug 12 to compress into. In this configuration, the plunger 30 is ready to deploy (i.e compress) the plug 12.

However, in some embodiments, it is contemplated that actuating the plunger 30 to the released position described above can automatically put the plunger 30 in a state ready to deploy the anchor 10, plug 12, filament 14, and locking element 16 and, in some cases, retract the implantation device 24 and insertion sheath 60 creating a gap for deployment, if desired.

Figure 10:
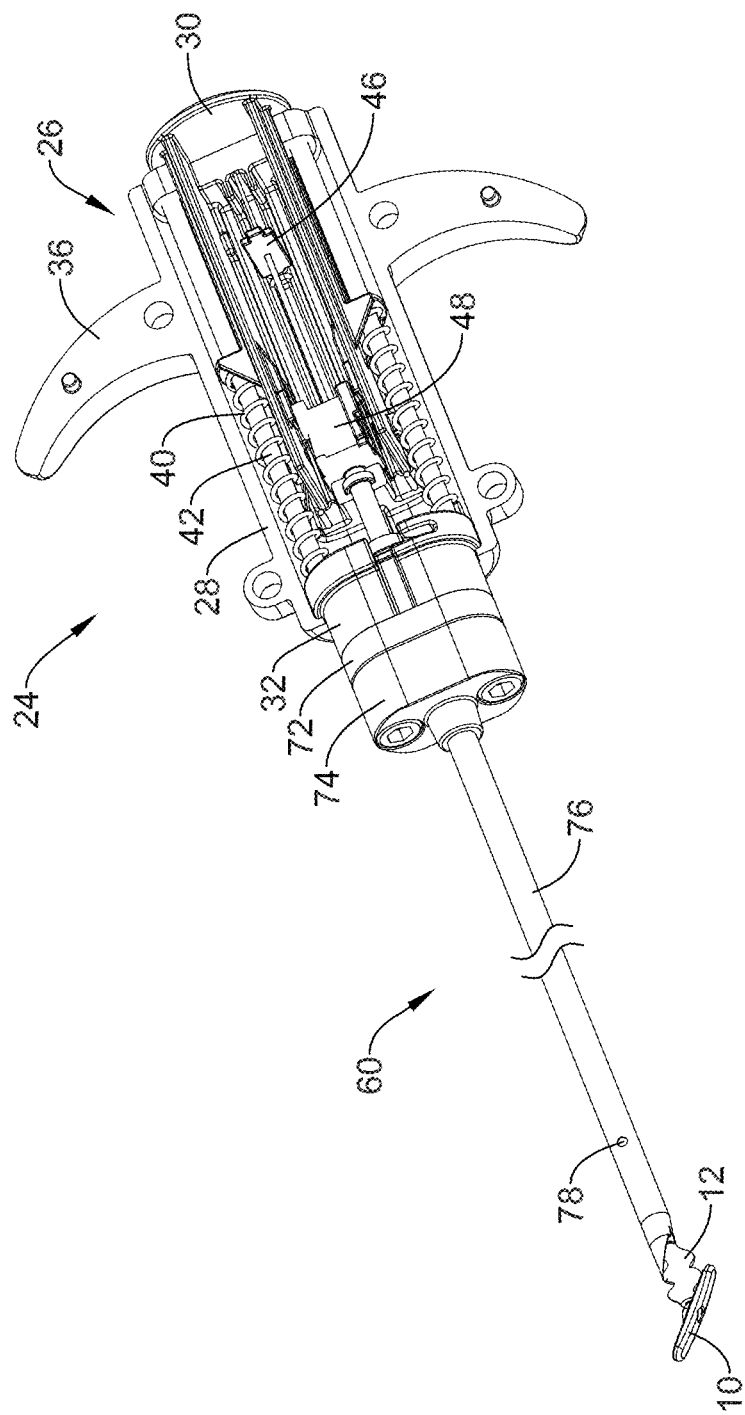
Figure 12:
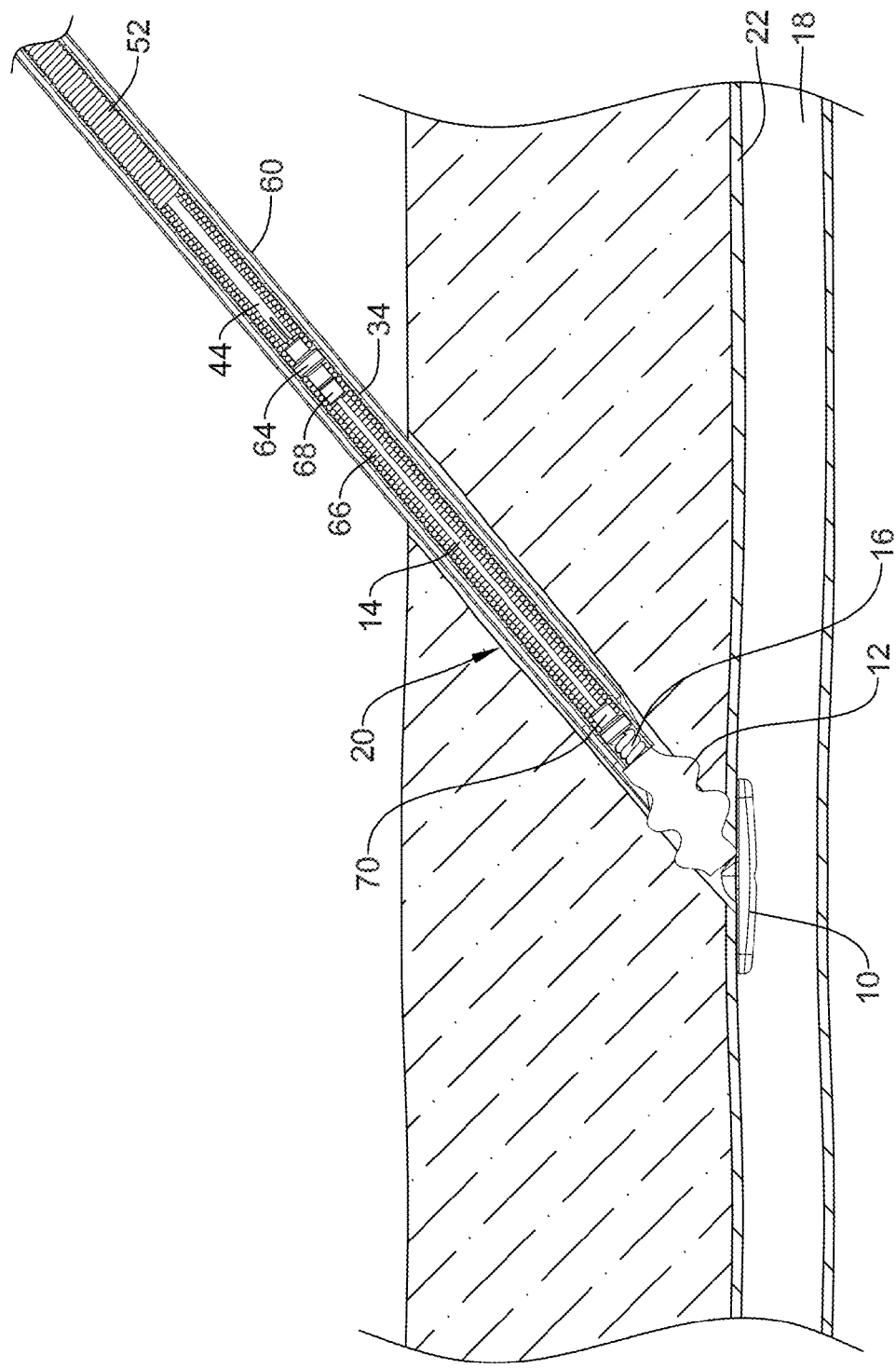

In FIG. 10, the plunger 30 has been be manually actuated distally, thereby advancing the proximal push rod 52 distally, which in turn may advance the filament release bead 64 distally, which in turn may advance the distal push rod 66 distally, which may advance the plunger compression bead 70 distally, which may advance the locking element 16 distally to axially compresses the plug 12, as can be seen in FIG. 12. When the plug 12 is deployed, the plug 12 may radially expand, as discussed above, and be coupled to the anchor 10 by locking element 16.

Figure 11:
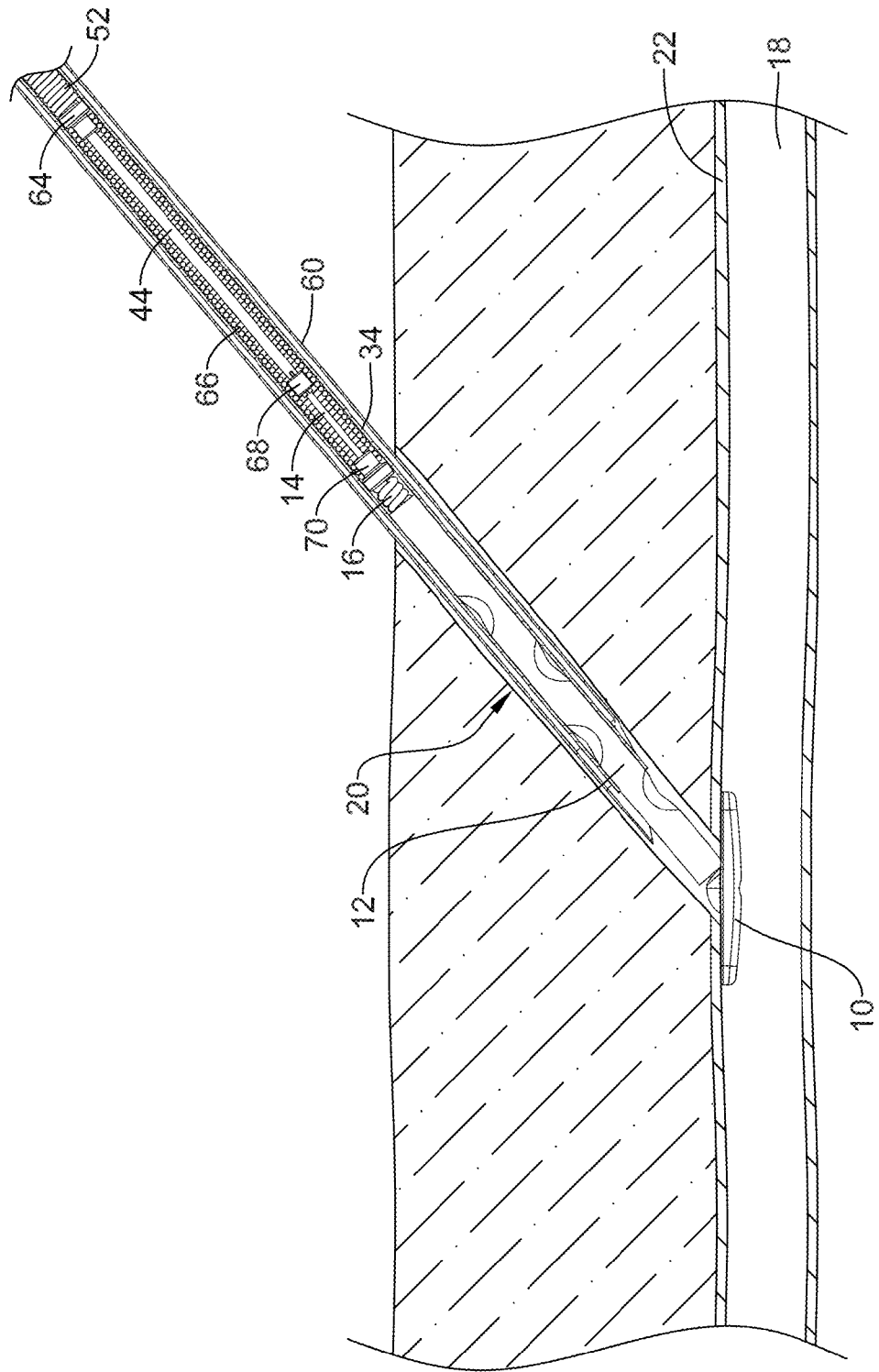
FIGS. 11-13 are schematic diagrams of illustrative embodiments of the automatic filament release mechanism of the implantation device.
Figure 13:
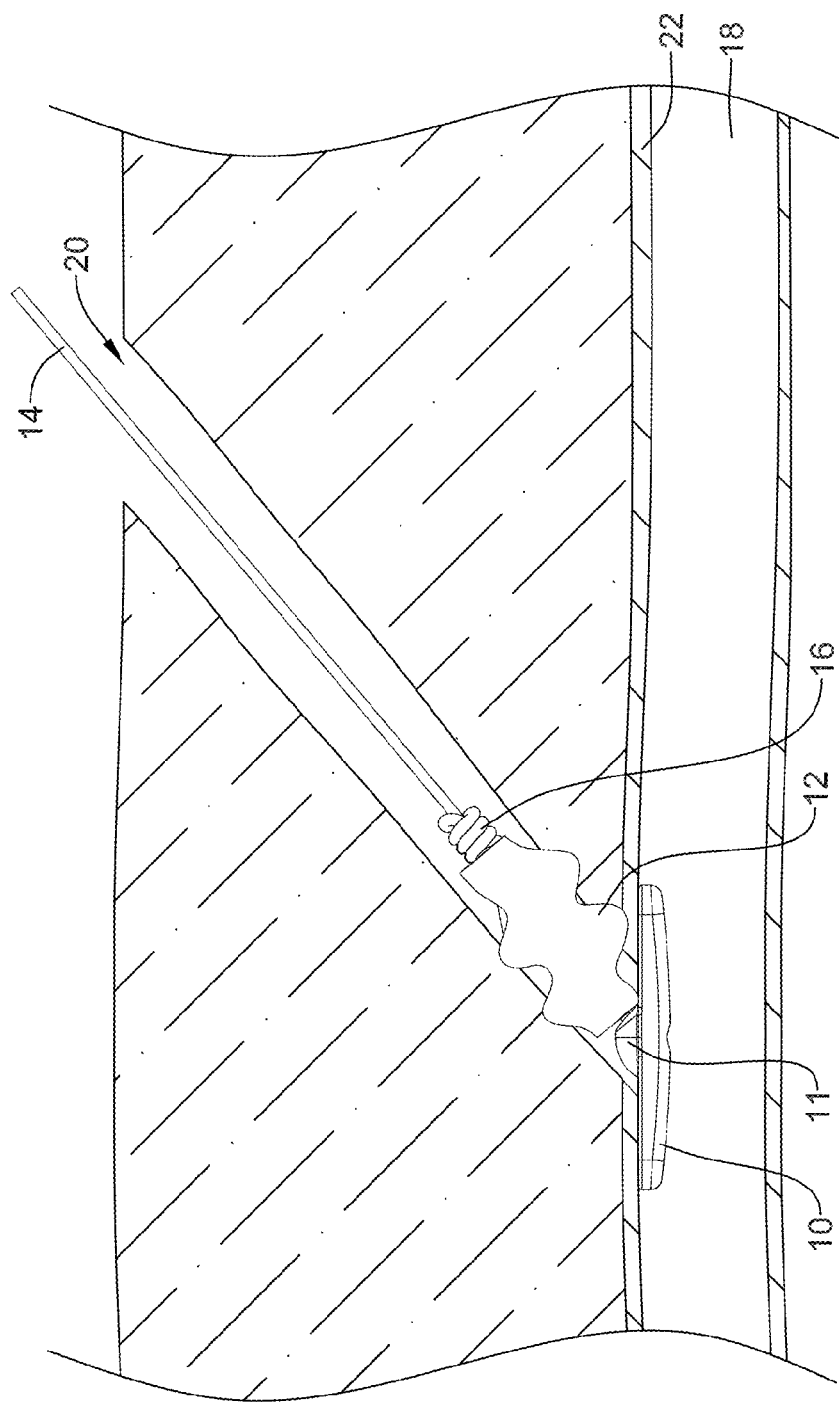

FIGS. 11-13 are schematic diagrams of illustrative embodiments of the automatic filament release mechanism of the implantation device distal end. In the illustrative embodiment, the automatic filament release mechanism can include a collet 44, a collet lock ring 68, and a filament release bead 64. As shown in FIG. 11, the insertion sheath 60 may be disposed at least partially in the tissue tract 20 for providing access to the opening in the vessel wall 22. The implantation device distal end may be inserted into the insertion sheath 60. As shown, the anchor 10 is seated against the interior of the vessel wall 22 or arteriotomy. The filament 14 is coupled to the anchor 10 and extends proximally through the tissue tract 20. The plug 12 is disposed over the filament 14 adjacent the anchor 10, and the locking element 16 is disposed about the filament 14 proximal of the plug 12. The plug 12, filament 14, and locking element 16 may be disposed, at least partially, within the implantation device sheath 34. The insertion sheath 60 and/or the device sheath 34 may be retracted a distance from the anchor 10 and/or opening in the vessel wall 22 to provide an area for deployment of the plug 12. In the illustrative example, the distance may be about one-quarter to three-quarters of the length of the plug 12. For example, if the plug 12 is about one inch long in a non-axially compressed state, the distance that the insertion sheath 60 and device sheath 34 can be retracted may be about one-quarter inch to about three-quarters of an inch. However, it is contemplated that any suitable distance may be used, as desired.

As illustrated in FIG. 11, the collet 44 can be coupled to the filament 14 by a collet locking ring 68. As the proximal push rod 52 is advanced distally, the filament release bead 64 may be advanced distally over the collet 44. The filament release bead 64 may engage the collet locking ring 68 and push the collet locking ring 68 off of the collet 44, as shown in FIG. 12, releasing the filament 14.

Simultaneously, the distal push rod 66 may advance the plunger compression bead 70 against the locking element 16 to compress the plug 12, as shown in FIG. 12. The plug 12 may be compressed and secured in the compressed state by the locking element 16. In one example, the locking element 16 may have a compressive force on the filament 14 creating a friction force in the locking element 16 of 0.5 pounds, 1 pound, 1.5 pounds, 2 pounds, or any suitable friction force, as desired. Accordingly, the force exerted by the plug compression bead 70 onto the locking element 16 may be greater than the friction force of the locking element 16. Further, the plug 12 may exert a rebounding force on the locking element 16 trying to return to the non-axially compressed position. However, the friction force of the locking element 16 may be configured to be greater than the rebounding force of the plug 12.

As shown in FIG. 13, the insertion sheath 60 of FIG. 12 and the implantation device 24 can be removed from the tissue tract 20 leaving the anchor 10, plug 12, filament 14, and locking element 16 to seal and/or close the puncture in the vessel wall 22.

In some cases, the filament 14 may stretch slightly when a tensioning force is applied in the proximal direction. With many devices, the magnitude of the tensioning force can result in varying size gaps for plug deployment. In the illustrative embodiment of FIGS. 11-13, the collet 44 and/or collet lock ring 68 may be configured to engage the filament 14 a short distance proximal of the locking element 16 (prior to deployment) to define a tensioned length of the filament 14. In this case, the tensioning force can be spread out only over the tensioned length of the filament 14. In one example, the collet 44 and/or collet lock ring 68 may engage the filament 14 less than one inch proximal of the locking element 16. For example, the collet 44 and/or collet lock ring 68 may engage the filament 14 one-quarter inch, one-half inch, three-quarter inch, one inch, or any other suitable length proximal of the locking element 16, as desired. This example may provide a length of filament 14 with a smaller amount of length to stretch than a filament that has a tensioning length extending into the device handle 26, which may provide for less variance in the size of the gap for plug 12 deployment. In another example, it is contemplated that the length of the filament 14 may terminate in the insertion sheath tube 76 and not in the device handle 26, but this is not required.

FIGS. 14A-J are perspective views showing an illustrative procedure for sealing and/or closing a puncture in a vessel wall 22 and/or adjacent tissue tract 20 using the implantation device 24 of FIG. 2. In some cases, a medical procedure can be preformed with a procedural sheath, which in some cases, may be different than the insertion sheath 60 described above. In this case, the procedural sheath may be swapped for the insertion sheath 60. In some cases, a guidewire may be used to facilitate the swapping. In some cases, the vessel may be occluded by depressing the skin to temporarily stop the flow of blood therethrough.

A dilator 90 can be provided in the insertion sheath 60 and over the guidewire 92. The dilator 90 may be configured to fluidly seal the distal end 80 of the insertion sheath 60 to inhibit the flow of blood therein. Similarly, the dilator 90 may be configured to tightly fit around the guidewire 92 to inhibit the flow of blood therein. In some cases, the dilator 90 and insertion sheath 60 may be assembled prior to insertion.

Figure 14A:
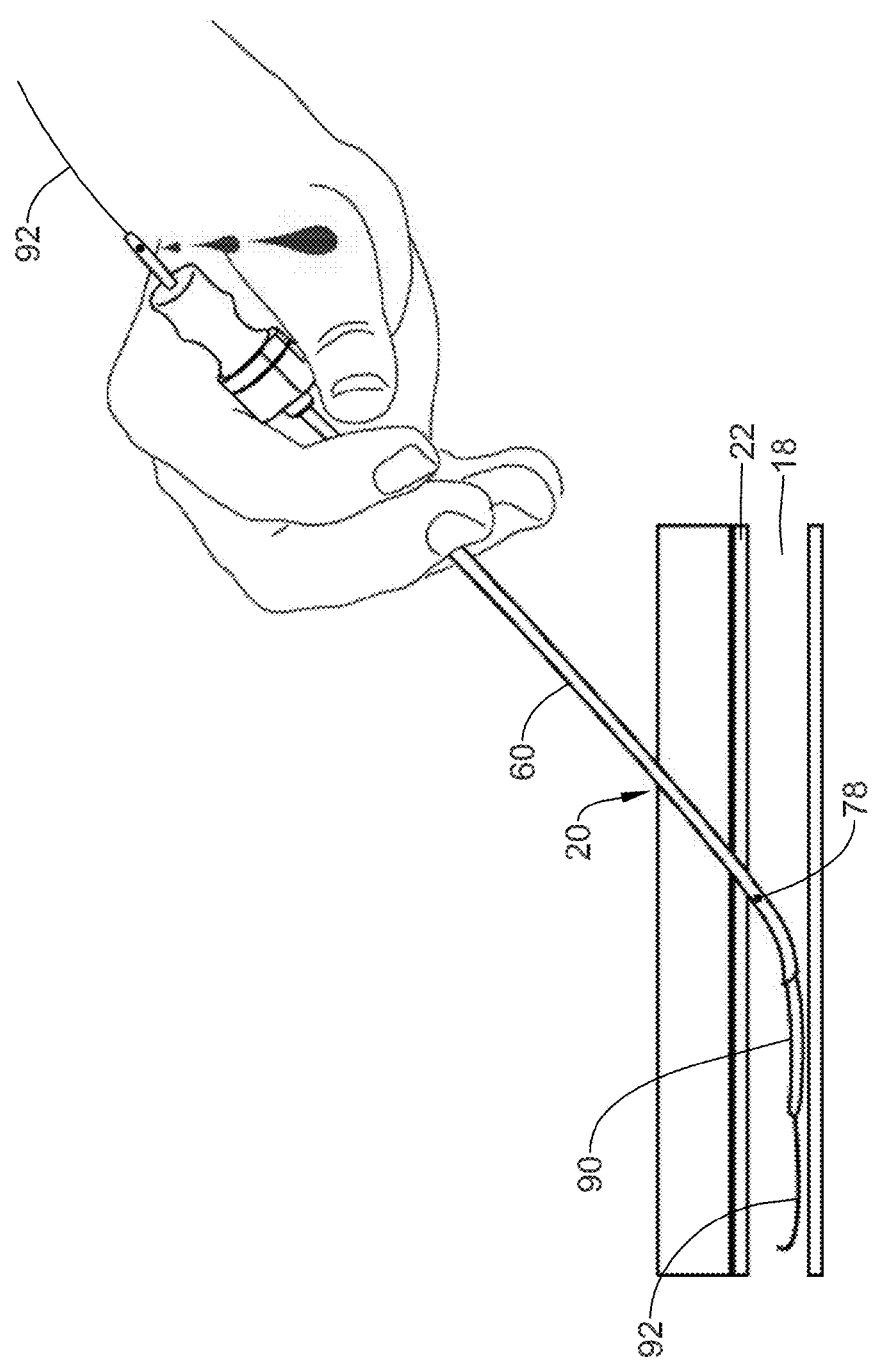

As shown in FIG. 14A, the opening 78 in the insertion sheath 60 and the dilator 90 may define a bleed path that may be used to identify the location of the distal end 80 of the insertion sheath 60. The insertion sheath 60 and dilator 90 combination can be withdrawn proximally until blood does not flow through the bleed path, as shown in FIG. 14B. Then the insertion sheath 60 and dilator 90 may be re-inserted into the blood vessel 18 until blood flow resumes, and the position of the insertion sheath may be maintained, as will be discussed in more detail below. In some embodiments, the opening 78 of the insertion sheath 60 may be aligned with the vessel wall 22. Once the proper position is located, the dilator 90 and guidewire 92 may be removed from the insertion sheath 60.

Figure 14C:
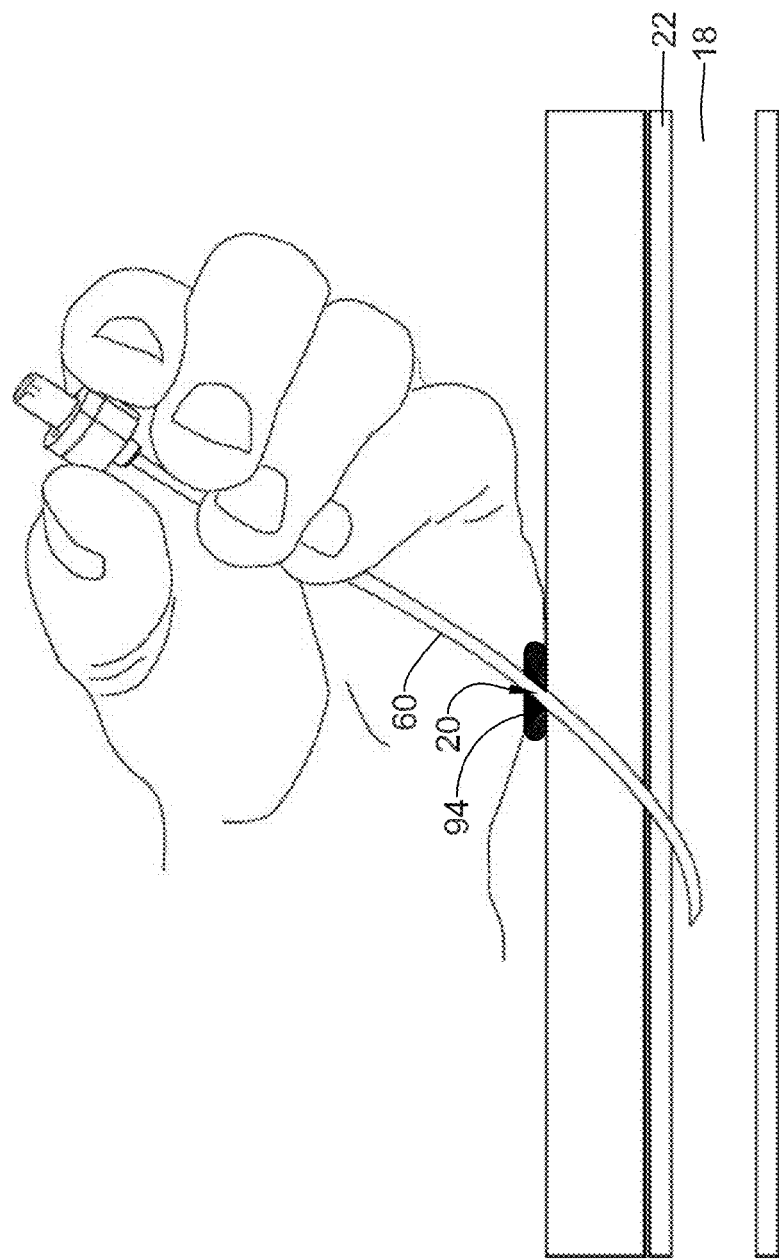

As shown in FIG. 14C, the insertion sheath 60 may be maintained in the located position. In some cases, an annular shaped locking ring 94 or other suitable locking ring, such as an elastomeric o-ring, can be used to maintain the position of the insertion sheath 60. In other cases, a physician or medical technician may hold the insertion sheath 60 to maintain the position. In some embodiments, an indicator or other visual mark can be provided to verify that the proper location is maintained.

Figure 14D:
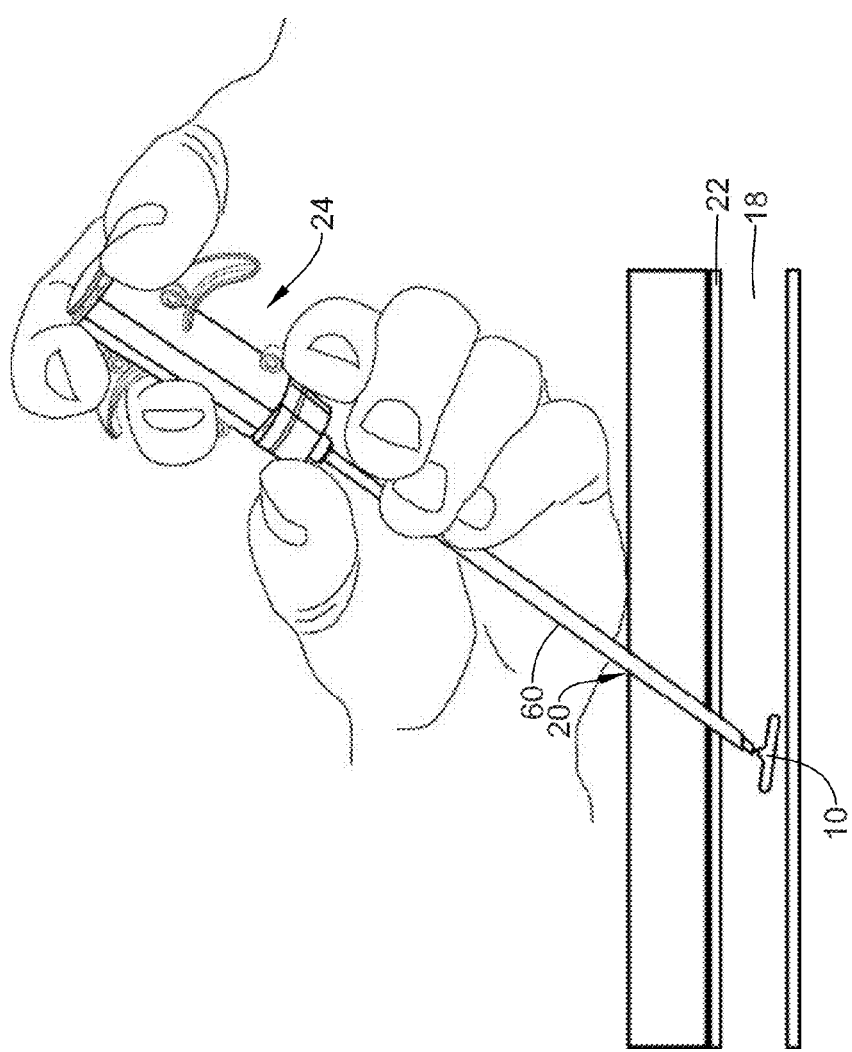

The implantation device 24 can then be inserted into the proximal end of the insertion sheath 60. In some cases, the bypass tube 62 can be used to load the anchor 10. Then, as shown in FIG. 14D, the implantation device 24 can be inserted through the hemostatic valve and connected to the insertion sheath 60. At the same time, the anchor 10 can be deployed into the vessel 18.

As shown in FIGS. 14D and 14E, the implantation device 24 can be rotated relative to the insertion sheath 60 to release the control handle connector 32 to seat the anchor 10 against the beveled distal end 80 of the insertion sheath 60. In some cases, the rotation can be a one-quarter turn. However, any suitable rotation can be used, as desired. Further, it is contemplated that non-rotational connection methods may be used, as desired.

Figure 14F:
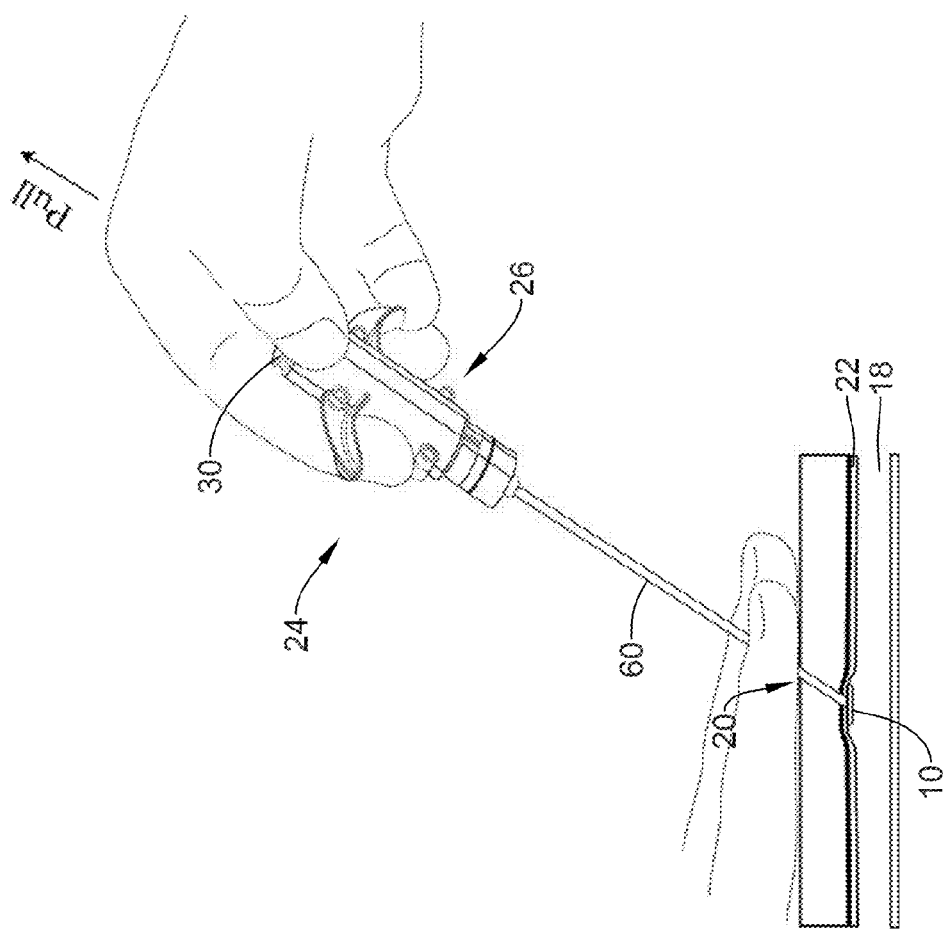

As shown in FIG. 14F, the device handle 26 and insertion sheath 60 can then be retracted proximally to seat the anchor 10 against the interior surface of the vessel wall 22. With the anchor 10 seated against the interior surface of the vessel wall 22, tension may be continually applied to the device handle 26 while pushing down on the plunger 30 to cause the plunger 30 to pop up when released, as shown in FIG. 14G.

Also, as shown in FIG. 14G, a continued tension on the device handle 26 can cause the implantation device 24 and the insertion sheath 60 to retract proximally exposing an area in the tissue tract 20 for the plug 12 to deploy into. While the implantation device 24 is retracted, the interlock block 48 may engage the ramp 47 of the plunger 30 (see FIGS. 8 and 9).

In FIG. 14H, the plunger 30 of the implantation device 24 can be depressed to deploy the plug 12 in the tissue tract 20 while continuing to apply tension to the implantation device 24. As shown in FIG. 14I, with continued tension to the implantation device 24, the plunger 30 can be completely depressed to actuate the automatic filament release mechanism to release the filament 14 from the implantation device 24.

Figure 14J:
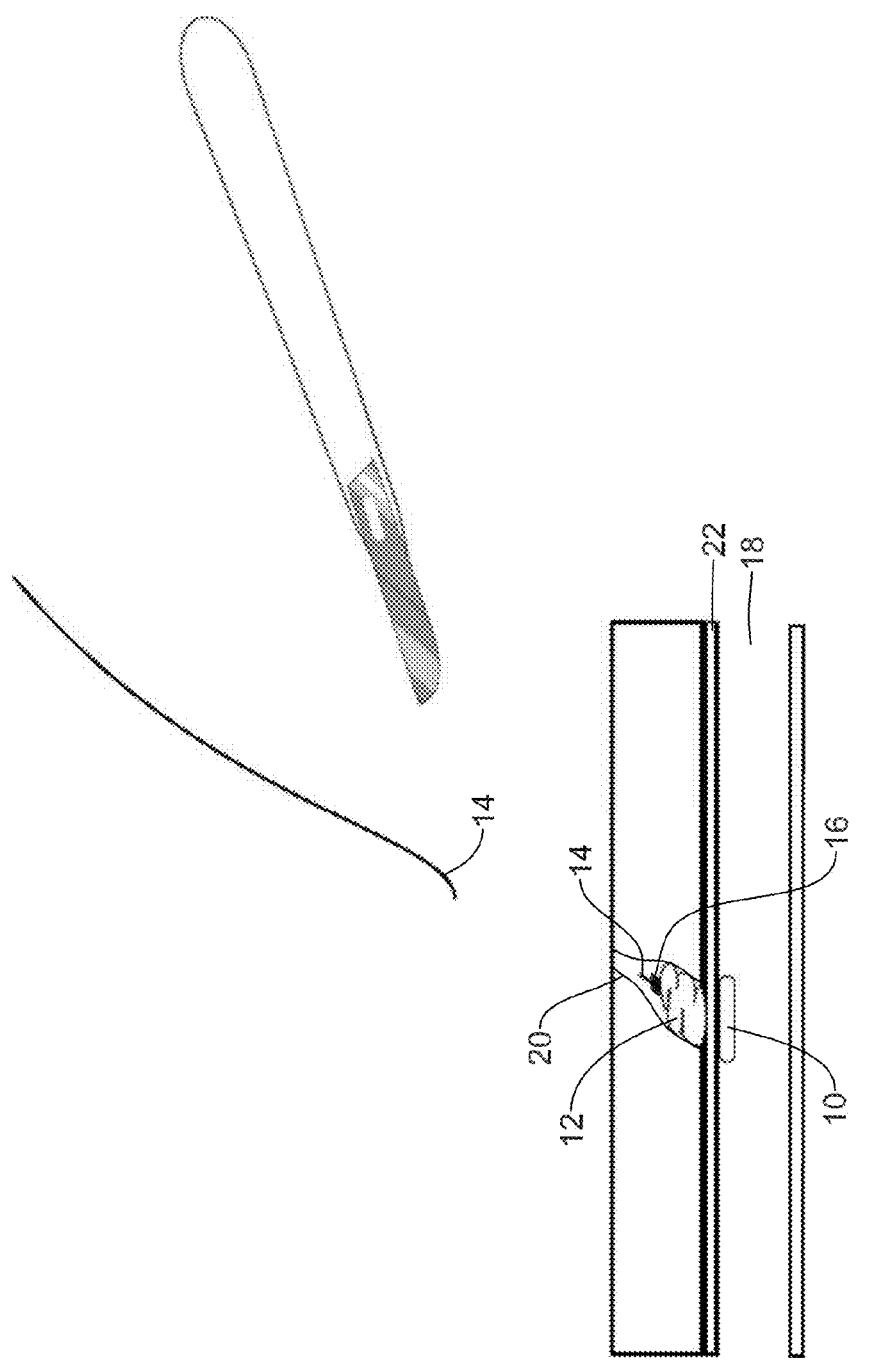

As shown in FIG. 14J, the filament 14 is released from the implantation device 24 and then, the insertion sheath 60 and implantation device 24 can be removed from the tissue tract 20 leaving the anchor 10, plug 12, filament 14, and locking element 16 to seal and/or close the opening in the vessel wall 22 and/or tissue tract 20. The length of the filament 14 extending proximally of the locking element 16 and/or outside of the tissue tract 20 can be removed, such as, for example, by cutting. In other cases, the filament 14 may have a length such that no cutting may be needed. When the plug 12 is exposed to a fluid, such as blood for example, the plug 12 can expand to fill the tissue tract 20 and/or opening in the vessel wall 22.

While the foregoing has described the implantation device 24 in detail, this is not meant to be limiting in any manner. It is contemplated that any suitable apparatus for sealing and/or closing an opening in a vessel wall 22 and/or tissue tract 20 can include any combination of the above-described features.

Other examples can include a plug 12, an anchor 10, a filament 14, and a locking element 16, as discussed above. In some cases, a device sheath 34 may include at least the filament 14, plug 12, and locking element 16 during introduction and the device sheath 34 may be attached to a device handle 26 at one end and having a tip at the other end, with the filament 14 releasably attached to the device handle 26. In some cases, an insertion sheath 60 may pass the plug 12, filament 14, anchor 10, locking element 16, and/or device sheath 34 through a tissue tract 20 to the artery, the insertion sheath 60 may have a hub 71 attached to one end. In some cases, a positioning guide may be used to properly position the tip of the insertion sheath 60 in the artery. In some cases, a locking mechanism may attach and hold the insertion sheath 60 hub 71 to the device handle 26 in proper alignment with the tip of the device sheath 34 and the anchor 10 extending out the distal end 80 of the insertion sheath 60. In some cases, a seating mechanism may be used to retract the device sheath 34 and the filament 14 to seat the anchor 10 against the tip of the device sheath 34. In some cases, a sheath retraction mechanism, which may retract the sheath(s) a controlled amount from the anchor 10 and may expose at least a portion of the plug 12, can be used. In some cases, an arming mechanism which may help prevent premature advancement of the plug 12 along the filament 14 until the arming mechanism is actuated can be used. In some cases, a plug 12 advancement mechanism, which may advance the plug 12 along the filament 14 to cinch the plug 12 towards the anchor 10 a controlled amount and may actuate the locking element 16 to hold the plug 12 in cinched configuration, may be used. In some cases, a filament 14 release mechanism which may release the filament 14 from the device handle 26 may be used.

Figure 15:
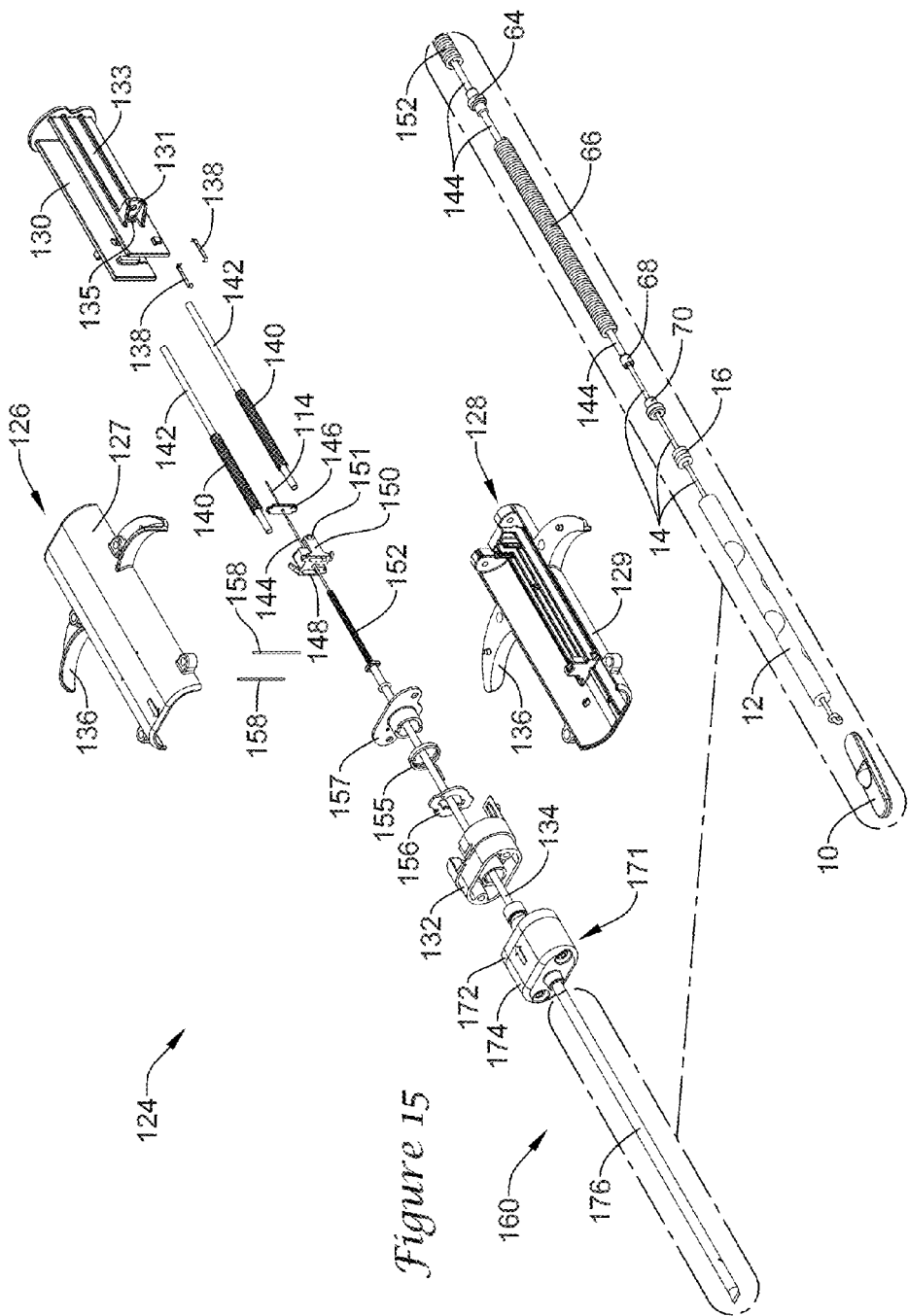
FIG. 15 is an exploded view of an illustrative embodiment of an implantation device.

FIG. 15 is an exploded view of an illustrative implantation device 124. In the illustrative embodiment, the device handle 126 can include a handle body 128, a plunger 130, a control handle connector 132, as well as a number of other components to aid in deploying anchor 10, plug 12, filament 14 and locking element 16 at a desired location. As illustrated, handle body 128 may be a composite body including a first half 129 and a second half 127 secured together with a fastener, adhesive, or other method, as desired. However, this is not meant to be limiting and it is contemplated that a suitable composite or a non-composite structure may be used, such as, for example, a body molded as a single piece, as desired. Similar to implantation device 24 described above, implantation device 124 may include one or more grip enhancement features, such as finger hooks 136, which may be similar in structure and function to finger hooks 36 described above. Plunger 130 may be configured to move relative to the handle body 128 to deploy the anchor 10, plug 12, filament 14, and locking device 16. In the illustrative example, the plunger 130 may move along one or more plunger guide pins 142, each of which may include an actuating spring 140 to bias the plunger 130 to a position outside of the handle body 128. The plunger guide pins 142 can be configured to have a free-floating first end, and a second end secured or mounted to the handle body 128. As illustrated, the plunger 130 may include a flange portion defining an opening 131 configured to receive the one or more plunger guide pins 142. Plunger 130 may also include ridges or ribs 133 disposed along a length of the plunger 130 configured to help stiffen the plunger 130 and aid in guiding the plunger 130.

In the illustrative embodiment, the plunger 130 may be initially retained within the handle body 128 to help prevent accidental or premature deployment of the plug 12 and locking element 16. To retain the plunger 130 in the handle body 128, a plunger protection mechanism including one or more plunger retainer clips 138 and one or more plunger retainer clip pins 158 can be provided. The one or more plunger retainer clip pins 158 can be secured to the handle body 128. The one or more plunger retainer clips 138 can have a proximal end secured relative to the plunger 130 and a distal end configured to engage the plunger retainer clip pins 158. In some cases, the distal end of the plunger retainer clip 138 can be curved to wrap at least partially around the one or more plunger retainer clip pins 158. In some cases, the one or more plunger retainer clips 138 can be biased radially outward so that when the plunger retainer clips 138 are moved in a proximal direction relative to the one or more plunger retainer clip pins 158, the plunger retainer clips 138 disengage the one or more plunger retainer clip pins 158 and spring outward allowing the plunger 130 to move in a proximal direction to a position at least partially outside of the handle body 128. In some cases, when the plunger retainer clips 138 disengage the one or more plunger retainer clip pins 158, the actuating springs 140 can bias the plunger 130 to move proximally out of the handle body 128.

The illustrative implantation device 124 can also include an interlock block 148 coupled to a proximal end of a proximal push rod 152. The interlock block 148 may also include one or more interlock block clips 150 having rounded protrusions 151 extending outwardly therefrom. Interlock block clips 150 may be integrally formed with interlock block 148, and may be formed from a polymer material. Interlock block clips 150 may be self-biased outwardly. The interlock block 148 and interlock block clips 150 may be configured to be disposed within the plunger 130 and to slide relative to the plunger 130 until the plunger 130 is withdrawn a distance proximally so that rounded protrusions 151 may engage one or more apertures 135 on the plunger 130.

As illustrated, a tubular member 144 can be provided having a proximal end disposed in the device handle 126 and a distal end disposed in the device sheath 134. In one example, the tubular member 144 can be a collet, but other suitable tubular members may be used, as desired. A proximal end of the collet 144 can be coupled to a retainer 146 configured to maintain the relative relationship of the collet 144 and handle body 128. The distal end of the collet 144 can include a collet lock ring 68 that is configured to have a releasable engagement with the filament 14. In some cases, the distal end of the collet 144 can be coupled to the proximal end of the filament 14. A filament release bead 64 can be disposed about a portion of the collet 144 a distance from the collet lock ring 68. The filament release bead 64 may slide relative to the collet 144 and is configured to engage the collet lock ring 68 and slide the collet lock ring 68 off of the collet 144 distal end releasing the filament 14.

A proximal push rod 152 can be disposed about at least a portion of the collet 144 between the interlock block 148 and the filament release bead 64. A distal push rod 66 can be disposed about the collet 144 and having a proximal end configured to engage the filament release bead 64 and a distal end configured to engage or couple a plug compression bead 70. The distal push rod 66 may be configured to slide over the collet lock ring 68. When the plunger 130 is actuated to deploy the plug 12 and locking element 16, the plunger 130 may engage the interlock block 148, which in turn may engage the proximal push rod 152, which in turn may engage the filament release bead 64, which in turn may engage the distal push rod 66, which in turn may engage the plug compression bead 70, which can engage the locking element 16, which can engage the proximal end of the plug 12. In this way, the force of the plunger 130 may be transferred to the locking element 16 to compress the plug 12. In some cases, the filament release bead 64 may simultaneously or concurrently pass over the collet 144 and engage the collet lock ring 68 to automatically release the filament 14 from the implantation device 124.

In the illustrative embodiment, the proximal push rod 152 and the distal push rod 66 may be a coil having a number of turns. However, it is contemplated that a suitable tubular member having a sufficient pushability and flexibility may be used, as desired.

The implantation device 124 may also include a control handle connector 132 configured to engage a hub 171 of the insertion sheath 160. The control handle connector 132 can be configured to be housed in the distal end of the handle body 128 or extend partially out of the distal end of the handle body 128. As illustrated, the control handle connector 132 may include a lumen configured to receive a proximal region of the device sheath 134. A keyed control disc 156 can be embedded in the control handle connector 132.

The device sheath 134 may be configured to be coupled to the distal end of the device handle 126 and extend distally therefrom. The device sheath 134 may include a thin-walled tubular member configured to house the collet 144, proximal push rod 152, filament release bead 64, distal push rod 66, collet lock ring 68, and plug compression bead 70. The device sheath 134 may also house the locking element 16, at least a portion of filament 14, and at least a portion of plug 12. The anchor 10 may be disposed adjacent to the distal end of the device sheath 134. As illustrated, a device sheath retainer may be configured to couple the device sheath 134 relative to the control handle connector 132 and/or device handle 126, similar to the embodiment illustrated in FIG. 3.

FIGS. 16-21 are perspective views and partial cut-away perspective views of the illustrative implantation device 124 in various stages of a procedure for implanting the anchor 10, plug 12, filament 14, and locking element 16 in the opening in a blood vessel wall and/or adjacent tissue tract.

Figure 16:
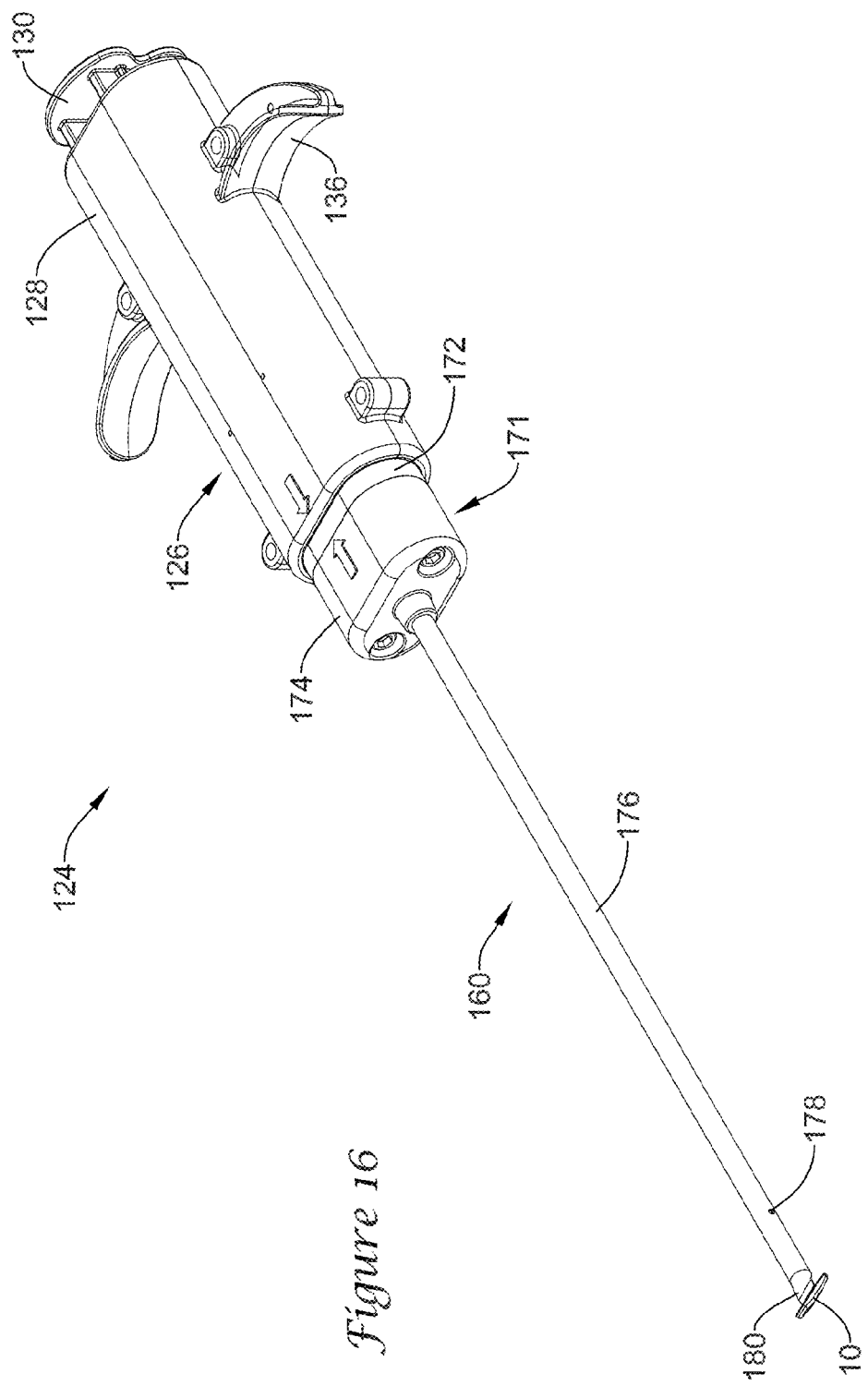

FIG. 16 is a perspective view of the illustrative implantation device 124 of FIG. 15 shown with insertion sheath 160 being connected to device handle 126. In the illustrative embodiment, the insertion sheath 160 may include a hub 171 and an insertion sheath tube 176. The hub 171 may be connected to a proximal end of the insertion sheath tube 176 and may include an insertion sheath connector 172, an insertion sheath cap 174, and a hemostatic seal (not shown) disposed between the insertion sheath connector 172 and insertion sheath cap 174. The insertion sheath connector 172 and insertion sheath cap 174 may be secured together with a fastener or adhesive, as desired. The hub 171 may have a lumen extending through the insertion sheath connector 172 and the insertion sheath cap 174. Alternatively, the hub 171 may be a single piece with a hemostatic seal disposed therein.

The insertion sheath tube 176 may include a thin-walled tubular member having a proximal end, a distal end, and a lumen extending therebetween. The proximal end of the insertion sheath tube 176 may be coupled to the hub 171 so that the lumen of the hub 171 is in fluid communication with the lumen of the insertion sheath tube 176. In some cases, the distal end 180 of the insertion sheath tube 176 may be beveled to accommodate the anchor 10 at the desired deployment angle for proper approximation to the artery.

In some cases, a position indicator, such as opening 178 may be positioned adjacent to the distal end 180 of the insertion sheath tube 176 to aid in positioning the insertion sheath 160 at a desired location in the vessel. In some embodiments, two openings 178 may be provided, each on an opposing side of the insertion sheath tube 176. The opening(s) 178 may provide an inlet for a bleed path which may flow through the insertion sheath 160 and/or a dilator to indicate the position of the insertion sheath 160 relative to the vessel wall opening. However, other suitable position indicators and/or locators may be used, such as, for example, one or more bent wires, one or more interlocking buttons, one or more folded components, an inflatable balloon, a radially expanding disc, as well as other suitable position indicator and/or locator or combination thereof, as desired.

In some cases, the insertion sheath 160 may include an orientation indicator on a proximal end thereof to help orient the insertion sheath 160. In some cases, the orientation indicator may be a line, mark, shape, other indicator, or combination thereof, to aid a user in orienting the insertion sheath 160 relative to its position in the vessel.

The device sheath 134 (not shown in FIG. 16) may be inserted in the proximal end of the lumen of the hub 171 and pass into the lumen of the insertion sheath tube 176. When the device sheath 134 enters the insertion sheath 160, the device sheath 134 may pass through and open the hemostatic seal of the insertion sheath 160. Implantation device 124 may or may not include a bypass tube, such as bypass tube 62 of FIGS. 3-5, which may be utilized in a similar manner to that described above.

Insertion sheath connector 172 and control handle connector 132 (not shown in FIG. 16) may include one or more protrusions or other orienting features that are configured to engage and/or align the insertion sheath connector 172 with the control handle connector 132 to mate the insertion sheath 160 to the implantation device 124. In an illustrative example, the control handle connector 132 of the device handle 126 may mate with the insertion sheath connector 172 in only one orientation. For example, the hub 171 may include a major radial axis that is aligned with a major radial axis of the device handle 126.

Figure 17:
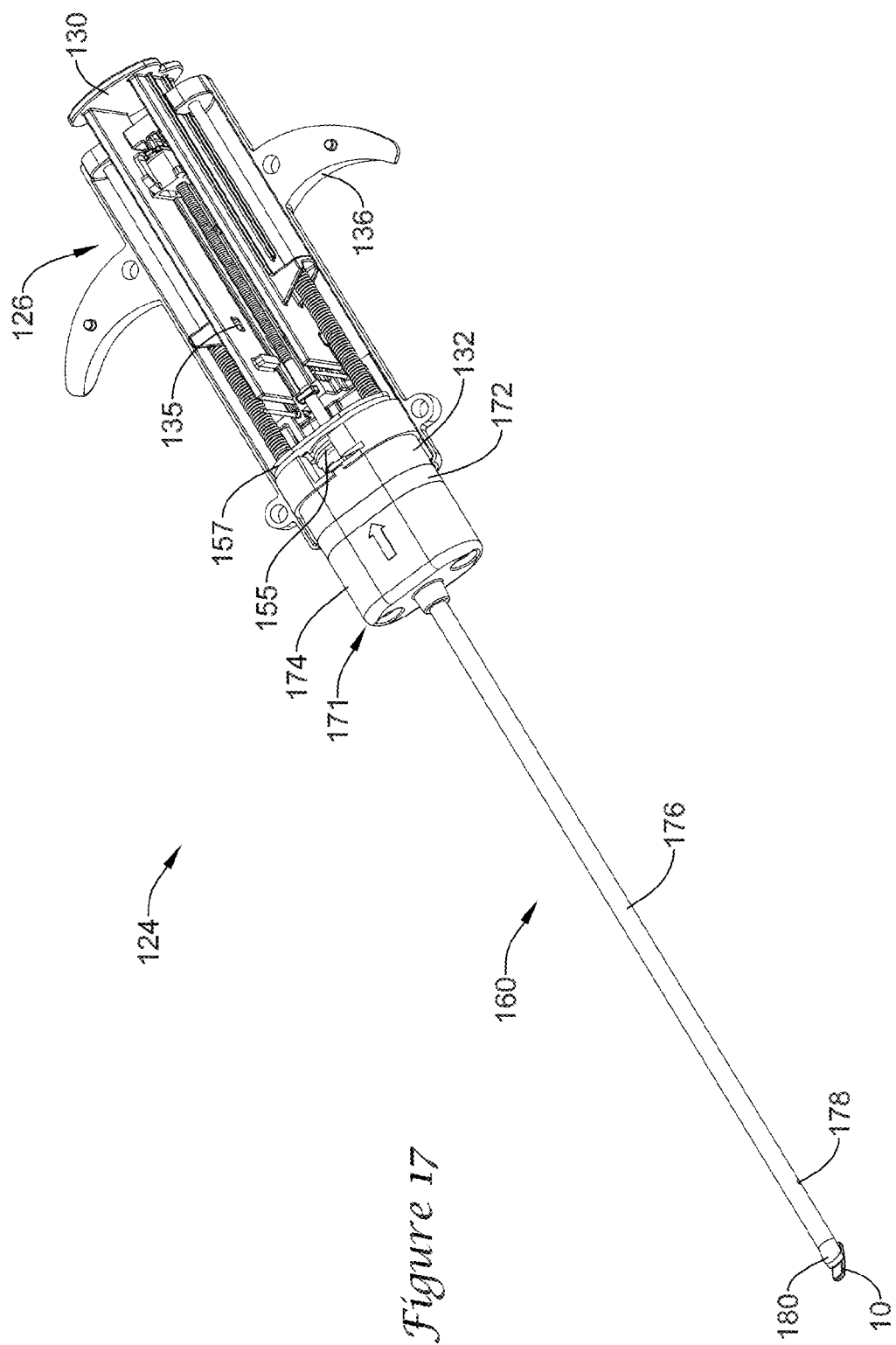

FIG. 17 is a partial cut-away perspective view of the illustrative implantation device 124 of FIG. 16 inserted in the insertion sheath 160, prior to actuation of a mechanism configured to lock hub 171 and insertion sheath 160 to control handle connector 132 and device handle 126. The mechanism may include a keyed control disc 156 (not shown in FIG. 17) disposed within the control handle connector 132, a torsion spring 155, and a torsion spring lock 157. The keyed control disc 156 cooperates with device handle 126 to maintain control handle connector 132 in a pre-seated position within device handle 126. Actuation of the mechanism will be described in more detail below.

In the illustrated example, the device sheath 134 (not shown in FIG. 17) of the implantation device 124 may be completely inserted into the insertion sheath 160. As also shown in FIG. 17, when the implantation device 124 is completely inserted, the anchor 10 can be deployed out the distal end 180 of the insertion sheath tube 176 into the vessel. When deployed, the anchor 10 may be initially spaced from the beveled distal end 180 of the insertion sheath tube 176, but, as shown in FIG. 18, can be subsequently retracted, in some cases automatically, against the beveled distal end 180.

Figure 18:
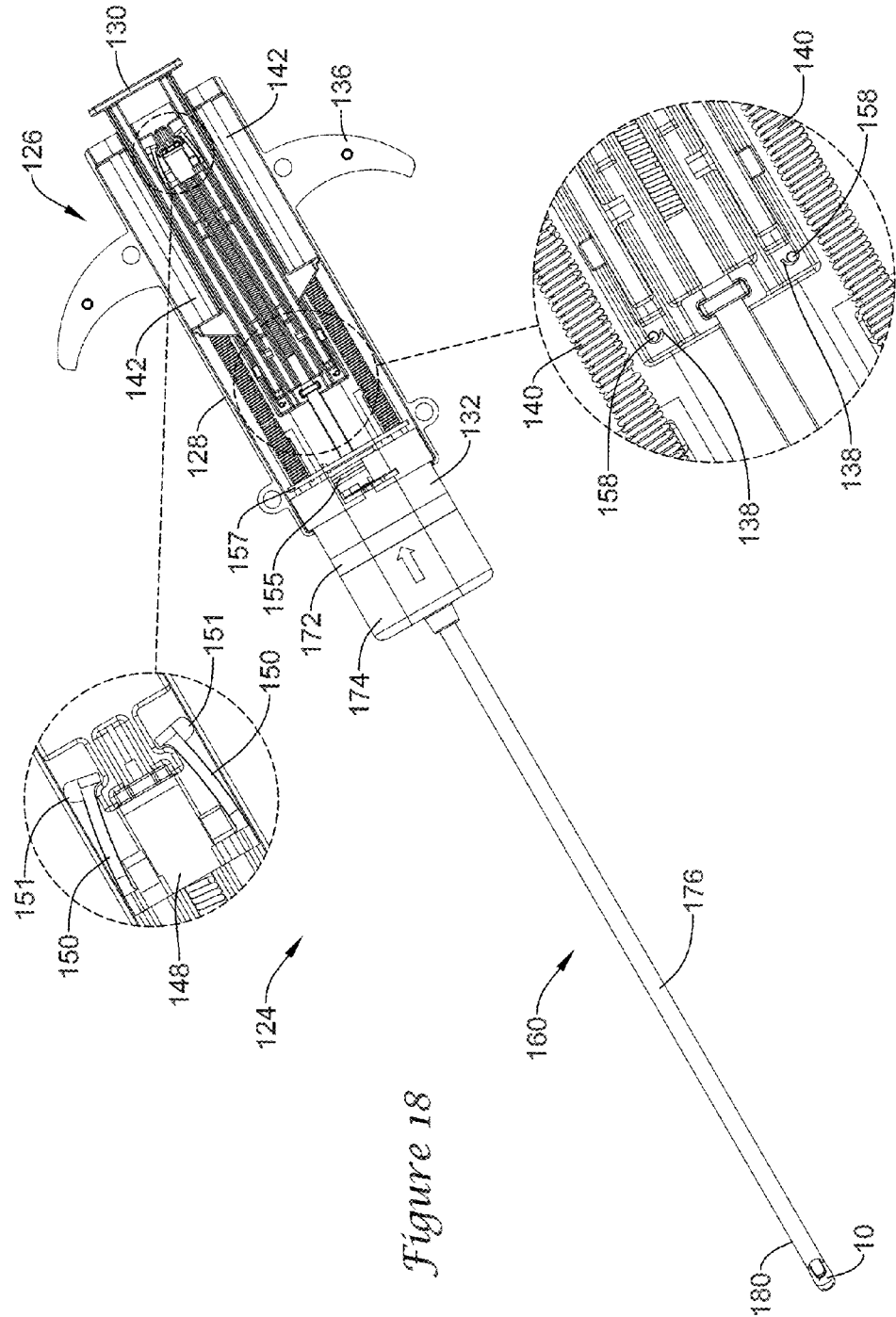

FIG. 18 is a partial cut-away perspective view of the illustrative implantation device 124 of FIG. 17 inserted in the insertion sheath 160 following actuation of the locking mechanism which occurs as a result of fully seating a proximal end of the insertion sheath 160 within the device handle 126. As illustrated, the implantation device 124 is secured to the insertion sheath 160. To do this, in one example, seating insertion sheath connector 172 within the control handle connector 132 can move the torsion spring lock 157 proximally, releasing the torsion spring 155 to rotate keyed control disc 156 (not shown in FIG. 18). Rotation of the keyed control disc 156 locks the implantation device 124 and the insertion sheath 160 together. Rotation of the keyed control disc 156 also releases the control handle connector 132 from the housing body 128 thus allowing actuating springs 140 to move the control handle connector 132 and the insertion sheath 160 a predetermined distance distally relative to the implantation device handle 126 (or moving the implantation device 124 a predetermined distance proximally relative to the insertion sheath 160), thereby automatically seating the anchor 10 against the beveled distal end 180 of the insertion sheath tube 176. However, it is contemplated that other attachment, alignment, and/or release mechanisms may be used to connect the insertion sheath 160 to the implantation device 124 and to seat the anchor 10 against the distal end of the insertion sheath 160, as desired. Examples of such components that may be used can include interlocking snaps, spring releases, keys, push pins, and any other suitable component, as desired.

As shown in the lower blown up portion of FIG. 18, the plunger retainer clips 138 may be engaged to the plunger retainer clip pins 158 retaining the plunger 130 in a retracted state to prevent premature deployment. The upper blown up portion of FIG. 18 shows rounded protrusions 151 on interlock block clips 150 compressed inwardly by the plunger 130. In this configuration, the plunger 130 may slide relative to the interlock block 148 without moving the interlock block 148.

Figure 19:
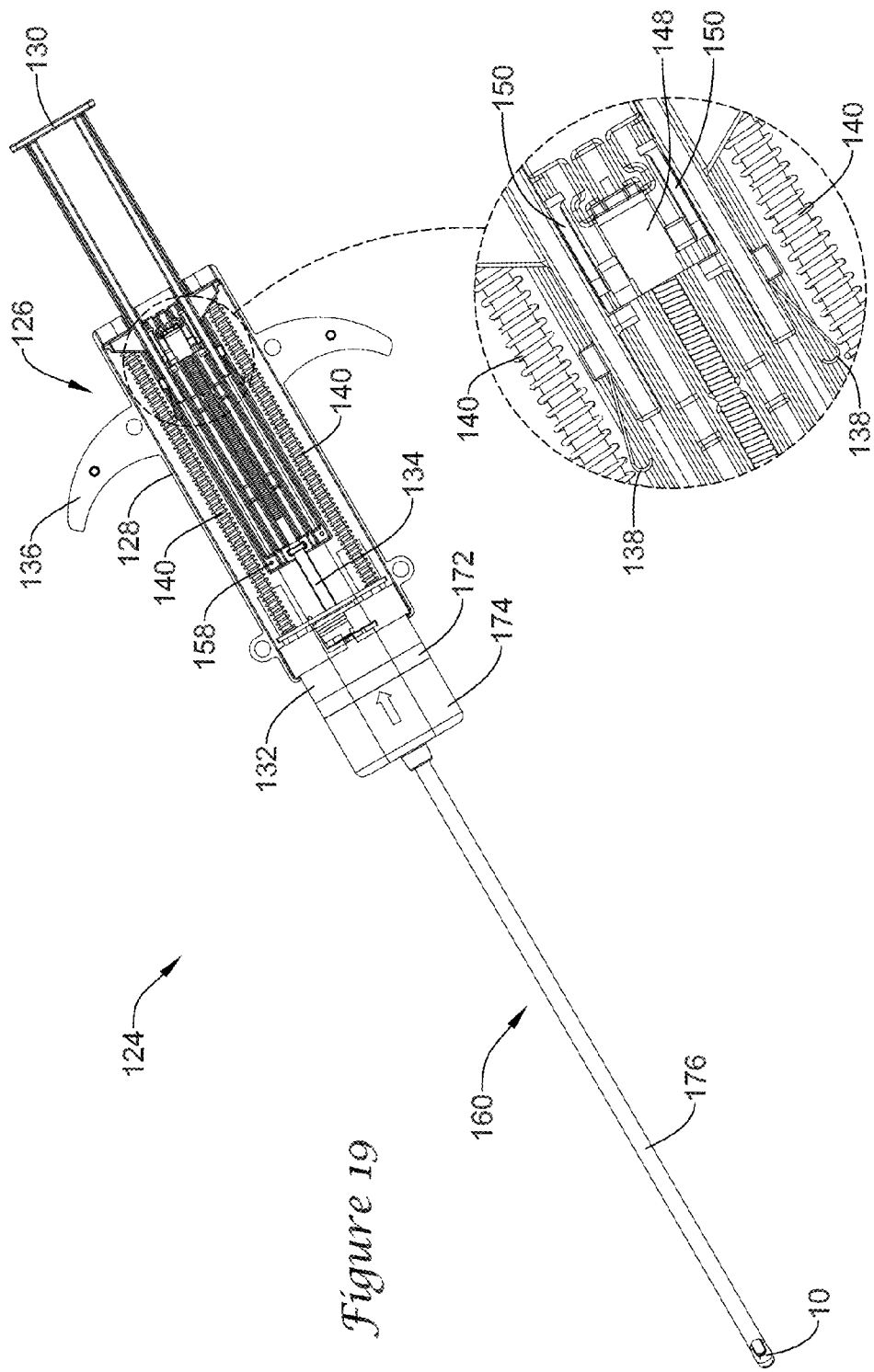

FIG. 19 is a partial cut-away perspective view of the illustrative implantation device 124 of FIG. 18 with the plunger 130 in a second, non-depressed position. In one example, to actuate the plunger 130 from the retracted state shown in FIG. 18 to the second non-depressed position of FIG. 19, the plunger 130 may be depressed at least slightly to a first depressed position causing the plunger retainer clips 138 (which may be self-biased radially outward) to disengage plunger retainer clip pins 158. When the plunger retainer clips 138 disengage the plunger retainer clip pins 158, the actuation springs 140 can cause the plunger 130 to move in a proximal direction. In some cases, the control handle connector 132 may hold the plunger retainer clips 138 against the plunger retainer clip pins 158 prior to being released from the handle body 128. However, the illustrative plunger protection mechanism including the control handle connector 132, plunger retainer clips 138, and plunger retainer clip pins 158 are merely illustrative and it is contemplated that other suitable plunger protection mechanisms may be used, as desired. Further, it is contemplated that in some embodiments, the plunger 130 can be automatically actuated to the second non-depressed position upon connection of the implantation device 124 to the insertion sheath 160 without the need for manual depression of the plunger 130, as desired.

As illustrated in FIG. 19, the plunger 130 is shown in the second non-depressed position, ready to deploy the anchor 10, plug 12, filament 14, and locking element 16 (elements 12, 14, and 16 are not shown in FIG. 19). In the illustrative embodiment, as noted above, the interlock block 148 and/or interlock block clips 150 may be configured to engage rounded protrusions 151 (not shown) with the apertures 135 (not shown) of the plunger 130 at the second non-depressed position. Interlock block 148 may also include one or more secondary clips (not shown) configured to engage the device handle 126 to prevent the interlock block 148 from moving proximally relative to the device handle 126.

Figure 20:
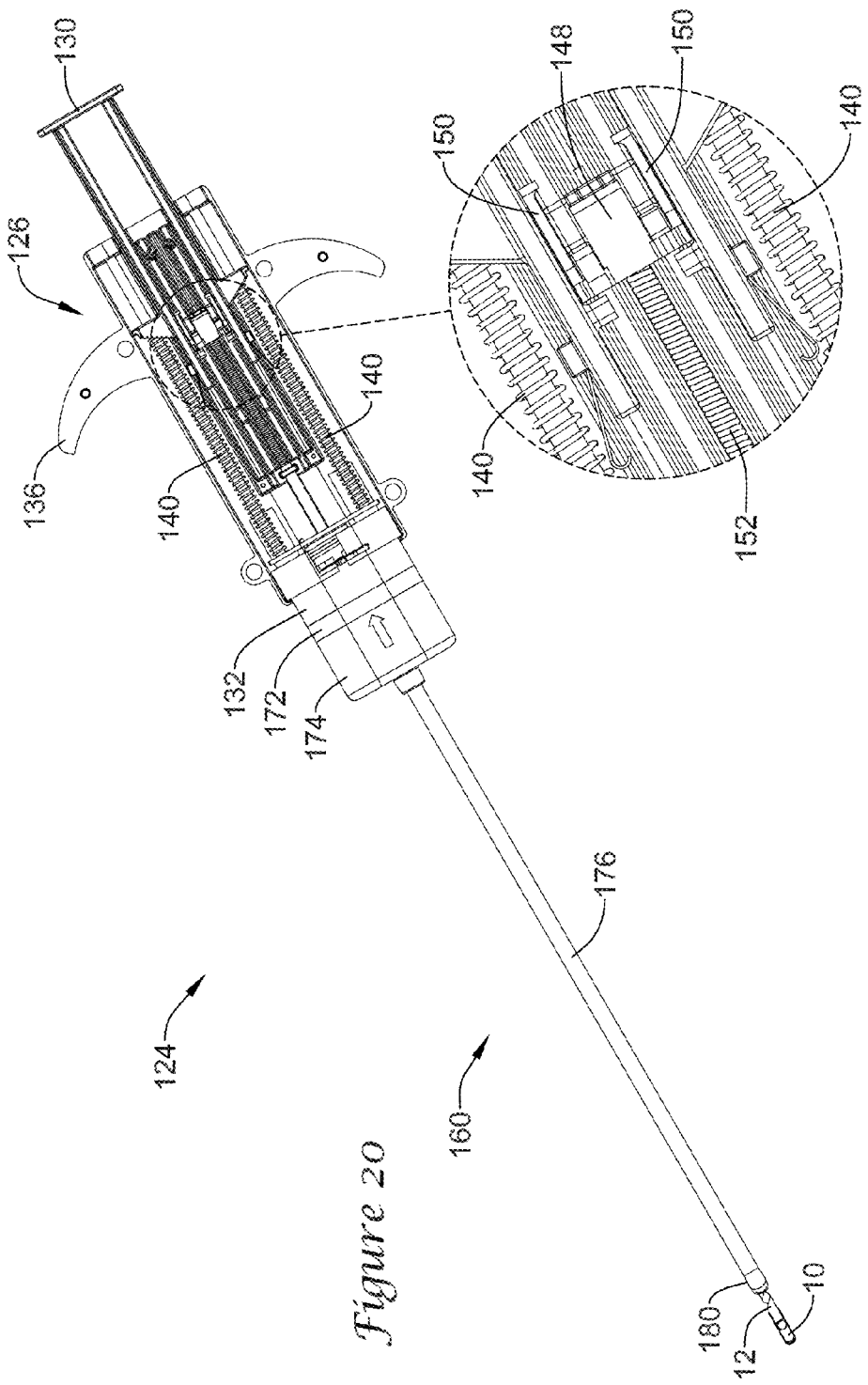

In the transition from the configuration of FIG. 18 to that of FIG. 19, the plunger 130 is moved proximally relative to the interlock block 148 and interlock block clips 150, causing the interlock block clips 150 to depress inward until the plunger 130 is moved proximally relative to the interlock block 148 so that the interlock block clips 150 may move radially outward, as shown in FIG. 19, to engage the apertures 135 (not shown). In some cases, this relative movement can be accomplished by applying tension to the device handle 126 of the implantation device 124 to retract the implantation device 124 and insertion sheath 160 in a proximal direction. The anchor 10 which is coupled to the filament 14 (not shown), which can be coupled directly or indirectly to the interlock block 148, can exert a counter force to the tension causing the interlock block 148 to slide distally relative to the device handle 126, as shown in FIG. 20. As also shown in FIG. 20, the tension or proximal retraction of the implantation device 124 can also create a gap between the distal end 180 of the insertion sheath 160 and the anchor 10 providing a place for the plug 12 to compress into. In this configuration, the plunger 130 is ready to deploy (i.e. compress) the plug 12.

Following engagement of the rounded protrusions 151 (see FIG. 18) with the apertures 135 (see FIG. 17), distal movement of the plunger 130 relative to the device handle 126 will cause the interlock block 148 to move distally relative to the device handle 126. At the same time, the one or more secondary clips, if present, may prevent the interlock block 148 from moving back in a proximal direction. Actuating the plunger 130 distally will also advance the proximal push rod 152 distally, which in turn may advance the filament release bead 64 (not shown) distally, which in turn may advance the distal push rod 66 (not shown) distally, which may advance the plunger compression bead 70 (not shown) distally, which may advance the locking element 16 (not shown) distally to axially compresses the plug 12. This may be illustratively seen in FIG. 21, which shows plug 12 compressed at a distal end 180 of insertion sheath 160 prior to release of filament 14 (not shown) from collet 144 (not shown).

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of sealing an opening in a vessel wall with an anchor, a filament, a locking element, and a plug comprising:
    inserting an insertion sheath through a tissue tract and into a vessel;
    coupling a distal end of the filament to the anchor, wherein a proximal end of the filament is coupled to an implantation device;
    disposing the plug about the filament proximal of the anchor;
    inserting a device sheath of the implantation device into the insertion sheath, the device sheath configured to house the filament and the plug prior to deployment, wherein the anchor is configured to pass through the insertion sheath to a position distal the insertion sheath when the device sheath is inserted into the insertion sheath;
    inserting a proximal end of the insertion sheath into a distal end of an implantation device handle as the device sheath is inserted into the insertion sheath;
    seating the proximal end of the insertion sheath within the implantation device handle to release a torsion spring disposed within the implantation device handle, wherein the torsion spring is configured to actuate a mechanism, wherein the mechanism automatically locks the insertion sheath to the implantation device handle and then automatically seats the anchor against a beveled distal end of the insertion sheath;
    positioning the anchor against an interior surface of the vessel wall adjacent to the opening;
    compressing the plug against the anchor;
    positioning the locking element adjacent to the plug; and
    releasing the filament from the implantation device, wherein the filament is automatically released when the plug has been compressed.

2. The method of claim 1, further comprising removing the insertion sheath and the device sheath from the tissue tract leaving the anchor, the plug, the filament and the locking element to seal the opening in the vessel wall.

3. A method of sealing and/or closing a tissue tract and/or opening in a vessel wall with an anchor, a filament, and a plug, the method comprising:
    providing an insertion sheath extending through the tissue tract and into a vessel;
    inserting a device sheath of an implantation device into the insertion sheath, the device sheath configured to house the anchor, the filament, and/or the plug prior to deployment, wherein the anchor is configured to pass through the insertion sheath to a position distal of the insertion sheath when the device sheath is inserted in the insertion sheath; and
    automatically seating the anchor against a beveled distal end of the insertion sheath wherein the automatically seating the anchor against the beveled distal end of the insertion sheath includes connecting a proximal end of the insertion sheath to a device handle of the implantation device and rotating a component of the device handle relative to the insertion sheath; and
    wherein the device handle further comprises a torsion spring locking element and a torsion spring engaged with a control disc; wherein inserting the device sheath into the insertion sheath disposes a proximal end of the insertion sheath within the device handle; wherein the proximal end of the insertion sheath is configured to engage the torsion spring locking element to release the torsion spring which thereby rotates the control disc within the device handle to lock the insertion sheath to the device handle.

4. The method of claim 3, wherein the device handle includes a plunger protection mechanism to prevent premature compression of the plug.

* * * * *